(12) United States Patent
Acher et al.

(10) Patent No.: US 9,212,196 B2
(45) Date of Patent: Dec. 15, 2015

(54) HYPOPHOSPHOROUS ACID DERIVATIVES HAVING ANTIHYPERALGIC ACTIVITY AND BIOLOGICAL APPLICATIONS THEREOF

(75) Inventors: Francine Acher, Vaucresson (FR); Jean-Philippe Pin, Montpellier (FR); Cyril Goudet, Saint Gely du Fesc (FR); Alain Eschalier, Chamalières (FR); Jérôme Busserolles, Saulzet (FR); Delphine Rigault, Viroflay (FR); Isabelle Lemasson, Paris (FR); Sara Cesarini, Paris (IT); Bruno Commare, Les Ventes Saint-Rémy (FR)

(73) Assignees: UNIVERSITE PARIS DESCARTES, Paris (FR); UNIVERSITE D'AUVERGNE, Clermont-Ferrand (FR)

( * ) Notice: Subject to any disclaimer, the term of this patent is extended or adjusted under 35 U.S.C. 154(b) by 0 days.

(21) Appl. No.: 14/118,379

(22) PCT Filed: May 16, 2012

(86) PCT No.: PCT/IB2012/052467
§ 371 (c)(1),
(2), (4) Date: Nov. 18, 2013

(87) PCT Pub. No.: WO2012/156931
PCT Pub. Date: Nov. 22, 2012

(65) Prior Publication Data
US 2014/0107078 A1    Apr. 17, 2014

Related U.S. Application Data

(60) Provisional application No. 61/486,785, filed on May 17, 2011.

(51) Int. Cl.
| | | |
|---|---|---|
| C07F 9/30 | (2006.01) |
| A61K 31/662 | (2006.01) |
| A61P 25/00 | (2006.01) |
| C07F 9/38 | (2006.01) |
| C07F 9/48 | (2006.01) |

(52) U.S. Cl.
CPC ............ C07F 9/3834 (2013.01); C07F 9/301 (2013.01); C07F 9/306 (2013.01); C07F 9/3808 (2013.01); C07F 9/4816 (2013.01)

(58) Field of Classification Search
CPC .............................. C07F 9/306; A61K 31/662
USPC ............................................ 514/140; 562/11
See application file for complete search history.

(56) References Cited

U.S. PATENT DOCUMENTS

2012/0016155 A1*    1/2012    Acher et al. .................... 562/11

FOREIGN PATENT DOCUMENTS

| WO | WO 2007/052169 | 10/2007 |
| WO | WO 2010/106526 | 9/2010 |

OTHER PUBLICATIONS

Williams et al. Foye's Principles of Medicinal Chemistry, 5th Edition, 2002, p. 59.*
Patani et al. Chemical Reviews 1996, 96, 3147-3176.*
International Search Report for PCT/IB2012/052467, mailed Jul. 23, 2012, (Jeanjean, Fabien).
Maier, L. et al., "Organic Phosphorus Compounds 761 Synthesis and Properties of Phosphinothricin Derivatives", Phosphorus and Sulfur and the Related Elements, vol. 17, (Jan. 1, 1983), pp. 1-20.

* cited by examiner

*Primary Examiner* — Sreeni Padmanabhan
*Assistant Examiner* — Irina Neagu
(74) *Attorney, Agent, or Firm* — Young & Thompson

(57) ABSTRACT

The invention relates to hypophosphorous acid derivatives of formula (I) wherein —X is H or OH, —R represents one or several radicals $R^1$-$R^5$, identical or different, two of $R^1$-$R^5$ optionally occupying the same position on the phenyl group, one to four of $R^1$-$R^5$ being H and the others being selected in the group comprising -O-$(CH_2)_n$—COOH; —S—$(CH_2)_n$—COOH; —NH—$(CH_2)_n$—COOH; -O-(CH,R')—COOH; —O—$(CH_2)_n$—OH; OR', —R' being a $C_1$-$C_3$ alkyl radical; —OH; —COOH; halogen, particularly —F, —Cl, —Br, —I, —$CF_3$; —$OCF_3$; —$NO_2$; —CH=CH—COOH; —$(CH_2)_n$—COOH; O—$(CH_2)_n$—$PO_3H_2$; O—$(CF_2)_n$—$PO_3H_2$; O—$(CH_2)_n$—$SO_3H$; O—$(CH_2)_n$—CONHOH; O—$(CH_2)_n$-tetrazol; O—$(CH_2)_n$-hydroxyisoxazol—n=1 to 5, preferably 1-3; said hypophosrous acid derivatives being diastereoisomers or enantiomers.

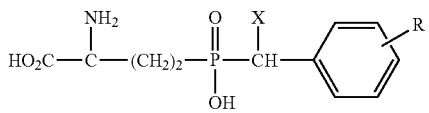

11 Claims, 7 Drawing Sheets

HYPOPHOSPHOROUS ACID DERIVATIVES HAVING ANTIHYPERALGIC ACTIVITY AND BIOLOGICAL APPLICATIONS THEREOF

This application is the U.S. national phase of International Application No. PCT/IB2012/052467, filed 16 May 2012, which designated the U.S., and claims the benefit from U.S. Provisional No. 61/486,785, filed 17 May, 2011, the entire contents of each of which are hereby incorporated herein by reference.

FIELD OF THE INVENTION

The invention relates to hypophosphorous acid derivatives having antihyperalgic activity and biological applications thereof.

BACKGROUND OF THE INVENTION

In WO 2007/052169, in the name of CNRS, inventors of the present application have disclosed hypophosphorous acid derivatives having agonist or antagonist properties for metabotropic glutamate receptors (mGluRs), particularly for group III, subtype 4 (mGlu4Rs), useful for treating neurodegenerative disease and brain disorders.

By pursuing their works in this domain, the inventors have now found that a specific group of the hypophosphorous acid derivatives disclosed in said WO application surprisingly have an agonist activity among the most powerful known on subtype 4 of the mGlu receptors and also are subtype 7 agonist of high value.

SUMMARY OF THE INVENTION

Accordingly, this is an object of the invention to provide a new group of hypophosphorous acid derivatives.

It is also an object of the invention to provide such derivatives for use as drugs, particularly for the treatment of neuropathic and inflammatory pain.

The hypophosphorous acid derivatives of the invention have formula (I).

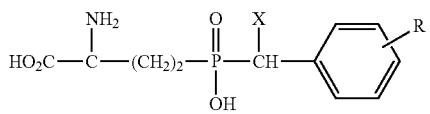

wherein
X is H or OH,
R represents one or several radicals $R^1$-$R^5$, identical or different, two of $R^1$-$R^5$ optionally occupying the same position on the phenyl group, one to four of $R^1$-$R^5$ being H and the others being selected in the group comprising —O—$(CH_2)_n$—COOH; —S—$(CH_2)_n$—COOH; —NH—$(CH_2)_n$—COOH; —O—(CH,R')—COOH; —O—$(CH_2)_n$—OH; OR', —R' being a $C_1$-$C_3$ alkyl radical; —OH; —COOH; halogen, particularly —F, —Cl, —Br, —I, —$CF_3$; —$OCF_3$; —$NO_2$; —CH=CH—COOH; —$(CH_2)_n$—COOH; O—$(CH_2)_n$—$PO_3H_2$; O—$(CF_2)_n$—$PO_3H_2$; O—$(CH_2)_n$—$SO_3H$; O—$(CH_2)_n$—CONHOH; O—$(CH_2)$-tetrazol; O—$(CH_2)$-hydroxyisoxazol
n=1 to 5, preferably 1-3; said hypophosphorous acid derivatives being diastereoisomers or enantiomers.

DETAILED DESCRIPTION OF THE INVENTION

As illustrated hereinafter in the Examples, the pharmacological peculiarity of the above compounds lies in their strong agonist activity on mGlu4R.

Depending on the substitutions, they may also be selective with respect to other metabotrobic receptors, particularly mGlu7 or mGlu8, resulting in specific properties.

They may thus have a higher agonist effect on mGlu7R compared to all known agonists, both subtypes mGlu4 and mGlu7 acting then in synergy for the treatment of pain. It will be measured that such a simultaneous activation has a high therapeutic interest.

In another embodiment, they may have mGlu8/4 $EC_{50}$ ratio of interest, particularly above 100.

Derivatives of a first preferred group have a $EC_{50}$ with respect to mGlu4≤0.2 1.1M.

Particularly preferred derivatives of said group also have a $EC_{50}$ with respect to mGlu7≤15 μM.

They include derivatives of formula (I) wherein X=—OH and R represents one substituent in para, or two substituents in meta and para, or three substituents, particularly two in meta and one in para, respectively.

In particularly preferred derivatives of said first group, the phenyl group is substituted by one substituent. A particularly preferred substituent is —O—$(CH_2)_n$—COOH with n=1 or —S—$(CH_2)_n$—COOH with n=1.

In other preferred derivatives of said first group, two substituents are present on the phenyl group, one being —O—$(CH_2)$, —COOH with preferably n=1, and the other is OR', with R' preferably being —$CH_3$ or $CF_3$.

In still other preferred derivatives, three substituents are present, one being —O—$(CH_2)_n$—COOH with preferably n=1, the second one is OR', with R' preferably being —$CH_3$ and the third one is —F, —Cl, —I or —$NO_2$.

Derivatives of a second preferred group have a $EC_{50}$ with respect to mGlu4< about 1 μM. They include derivatives of formula (I) wherein X=—OH or H and R represents one substituent in para, or two substituents in meta and para, or three substituents, particularly two in meta and one in para, respectively.

In particularly preferred derivatives of said second group, the phenyl group is substituted by one substituent. A particularly preferred substituent is —O—$(CH_2)_n$—COOH with n=1 and X=H; or —O—$(CH_2)_n$—$PO_3H_2$ with n=1 and X=—OH; or —$(CH_2)_n$—COOH with n=2 and X=—OH; or —CH=CH—COOH and X=—OH.

In other preferred derivatives of said second group, two substituents are present on the phenyl group, one being —O—$(CH_2)_n$—COOH with preferably n=1, and the other is OR', with R' preferably being —$CH_3$, or is OH, or is $NO_2$; or one is S—$(CH_2)_{n1}$—COOH with preferably n1=1 and the other is $NO_2$.

In other preferred derivatives, three substituents are present, one being —O—$(CH_2)_n$—COOH with preferably n=1 and the two others, identical or different, being selected from R as above defined or OR', with R' preferably being —$CH_3$, or —$NO_2$, —F, —Cl, or —I.

More particularly, the invention thus relates to the simultaneous activation of mGluR subtypes 4 and 7 for the treatment of neuropathic and inflammatory pain comprising using an effective therapeutic amount of said derivatives.

Other derivatives of interest have a $EC_{50}$ with respect to mGluR7 receptors above 15 μM, even above 100 μM. They correspond to derivatives having a high selectivity for mGluR4.

Other derivatives of high value have a high selectivity with respect to mGlu8 with $EC_{50}$ mGlu8>10/$EC_{50}$ mGlu4<0.5.

The invention thus also relates to pharmaceutical compositions comprising an effective amount of at least one of the hypophosphorous acid derivatives such as above defined in combination with a pharmaceutically acceptable carrier.

Advantageously, the pharmaceutical compositions of the invention are under a form suitable for an administration by the oral route, such as tablets, pills or capsules.

They preferably comprise 1 to 100 mg of active ingredient per dose unit.

Alternatively, the pharmaceutical compositions of the invention are under a form suitable for an administration by injection, such as injectable solutions for the intravenous, subcutaneous or intramuscular route. Such compositions advantageously comprise 1 to 30 mg of active ingredient per dose unit.

The invention also relates to a method for treating neuropathic and inflammatory pain comprising simultaneously activating glutamate metabotropic receptors sub-groups 4 and 7 by administering to a patient in need thereof an efficient amount of at least one hypophosphorous acid derivative of formula (I) as above defined.

The derivates of the invention are advantageously obtained by using the methods disclosed in above mentioned WO 2007/052169.

BRIEF DESCRIPTION OF THE DRAWINGS

Other characteristics and advantages of the invention are given in the following Examples with reference to FIGS. 1-5, which represent, respectively.

EXAMPLE 1

Experimental Part

Scheme 1

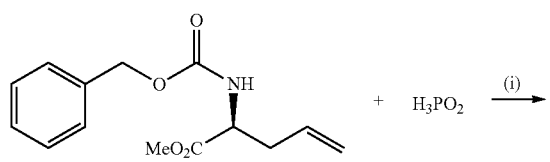

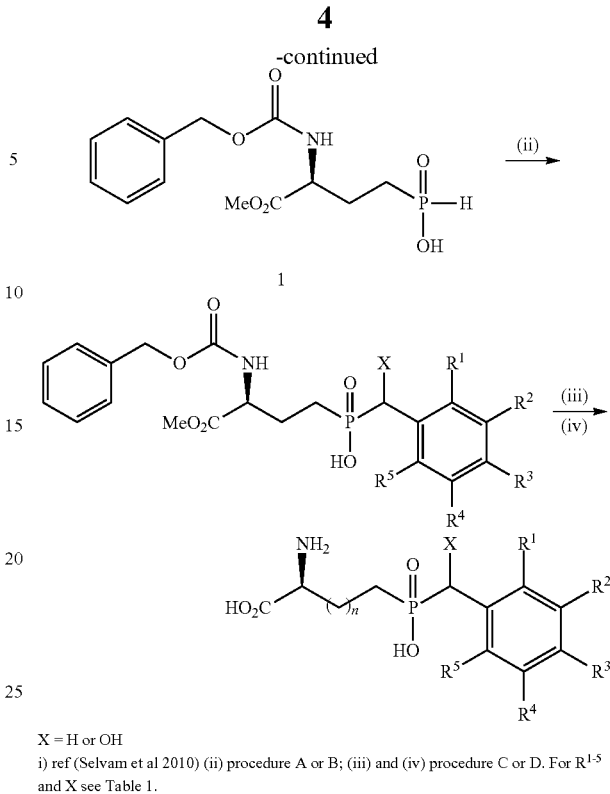

Figure 1:
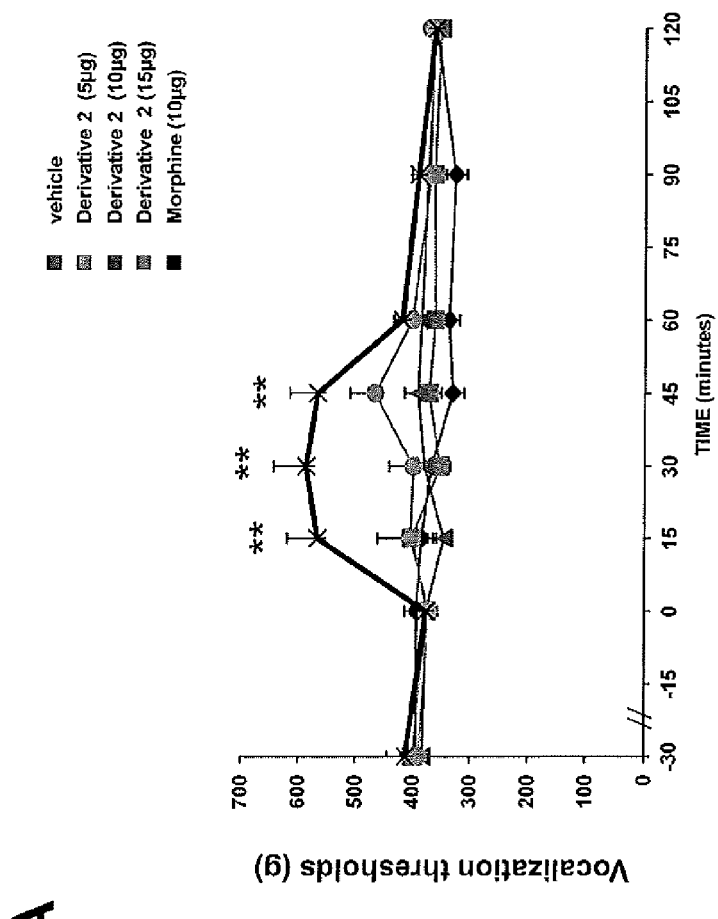
FIG. 1: the lack of effect of intrathecal administration of derivative 1 in healthy rats when pain is evoked by a mechanical stimulus.

X = H or OH i) ref (Selvam et al 2010) (ii) procedure A or B; (iii) and (iv) procedure C or D. For $R^{1-5}$ and X see Table 1.

General.

All chemicals and solvents were purchased from commercial suppliers (Acros, Aldrich) and used as received. Z-L-vinyl glycine methyl ester was purchased from Ascent Scientific Ltd (North Somerset, UK). Solvents for reactions were dried on 4 Å molecular sieves (Carlo Erba SDS). $^1$H (250.13 or 500.16 MHz), $^{13}$C (62.9 or 125.78 MHz) and $^{31}$P (101.25 or 202.47 MHz) NMR spectra were recorded on an ARX 250 or an Avance II 500 Bruker spectrometer. Chemical shifts (δ, ppm) are given with reference to residual $^1$H or $^{13}$C of deuterated solvents (CDCl$_3$ 7.24, 77.00; CD$_3$OD 3.31, 49.0; D$_2$O 4.80) or external reference (H$_3$PO$_4$ 95%). Product visualization was achieved with 2% (w/v) ninhydrin in ethanol. Thin layer chromatography (TLC) system for routine monitoring the course of certain reactions and confirming the purity of analytical samples employed aluminium-backed silica gel plates (Merck DC Kieselgel 60 F$_{254}$): CH$_2$Cl$_2$/MeOH or cyclohexane/ethyl acetate were used as developing solvents and detection of spots was made by UV light and/or by iodine vapours. Merck silica gel (230-400 mesh) was used for flash chromatography. Optical rotations were measured at the sodium D line (589 nm) at room temperature with a Perkin-Elmer 341 polarimeter using a 1 dm path length cell. Mass spectra (MS) were recorded with a LCQ-advantage (ThermoFinnigan) mass spectrometer with positive (ESI+) or negative (ESI−) electrospray ionization (ionization tension 4.5 kV, injection temperature 240° C.). HPLC analyses were carried out on a Gilson analytical instrument with a 321 pump, column temperature of Crownpak columns was controlled with an Igloo-CIL Peltier effect thermostat, eluted peaks were detected by a UV-vis 156 detector and retention times are reported in minutes. Two columns were used on analytic scale: a Daicel Crownpak CR(+) column (150 mm×4 mm), further designed as "Crownpak", eluted with pH 2.0 perchloric acid at a 0.4 mL·min$^{-1}$ flow rate, and a Phenomenex RP Polar column (250 mm×4.6 mm, 4 μm), further designed as "RP Polar", eluted at a 0.5 mL·min$^{-1}$ flow rate with the following method: solvent A: water/formic acid 1000:1, solvent B: water/acetonitrile/formic acid 900:100:1, 100% A for 10 min, linear gradient to 100% B from 10 to 30 min, 100% B from 30 to 40 min. Preparative scale HPLC was performed with a Daicel Crownpak CR(+) 150×10 mm column, further designed as "Preparative Crownpak", eluted with a pH 2.0 hydrochloric acid aqueous solution. HPLC-MS analyses were performed on a Thermo Finnigan LCQ Advantage Instrument as described above, equipped for HPLC with a Phenomenex RP Polar column (250 mm×4.6 mm, 4 μm). Products were eluted with the following gradient using solvent A (water/acetonitrile/formic acid 950:50:1) and solvent B (water/acetonitrile/formic acid 900:100:1), 100% A for 10 min, linear increase from 0 to 100% B between 10 and 20 min, 100% B from 20 to 30 min. Purity of the tested compounds was established by analytical HPLC-MS or by HPLC and was at least 95%.

[((3S)-3-(N-Benzyloxycarbonyl)amino-3-methoxycarbonyl)propyl]phosphinic Acid (1)

1 was synthesized according to previously published procedure. (WO2007/052169, Selvam et al JMedChem 2010).

General Procedure A:

To a solution of H-phosphinic acid 1 (1.0 mmol, 1 eq) and aldehyde (X=OH) or halide (X=H) (2.2 eq) in 2.0 mL of dichloromethane at 0° C. under an argon atmosphere was added dropwise N,O-bis(trimethysilyl)acetamide (BSA) (4.4 eq). The mixture was allowed to warm to room temperature and stirred overnight, then cooled to 0° C. and 25 mL of 1N HCl were added, then extracted with ethyl acetate. The organic layer was concentrated in vacuo. This residue was dissolved in 10 mL of water, the pH was adjusted to 7 using saturated sodium hydrogenocarbonate solution, then extracted with ethylacetate (2×50 mL). The organic layer was separated, and the aqueous phase was treated with aqueous HCl to adjust the pH to 1. The aqueous phase was extracted with ethyl acetate (2×50 mL). The combined acidic organic extracts were dried over magnesium sulfate, filtered and concentrated in vacuo.

General Procedure B:

To a solution of 1.0 mmol of H-phosphinic acid 1 and 2.2 mmol of aldehyde (X=OH) or bromide (X=H) in 2.0 mL of dry dichloromethane at 0° C. under argon was added dropwise N,O-bis(trimethylsilyl)-acetamide (BSA, 1.08 mL, 4.4 mmol). The mixture was allowed to warm to room temperature and stirred overnight under argon, then cooled to 0° C. 1N hydrochloric acid (20 mL) was added, then extracted with ethyl acetate (2×100 mL). The combined organic extracts were dried over magnesium sulfate, filtered and concentrated under vacuum. The crude product, still containing aldehyde or bromide in excess, was directly deprotected.

General Procedure C:

The crude product synthesised by general procedure A or B was dissolved in 6N hydrochloric acid (10.0 mL). The mixture was stirred at 100° C. for 5 h, then cooled to room temperature. The solution was diluted with ethyl acetate (50 mL) and water (10 mL). The separated organic layer was extracted with 1N hydrochloric acid (3×10 mL). The combined aqueous phases were concentrated under vacuum, then the residue was purified using a Dowex AG 50W-X4 cation exchange resin column (H$^+$, 50-100 mesh, water or 1N NH$_4$OH elution). If necessary, another purification was made on an anion exchange chromatography (Dowex AG 1-X4, AcO$^-$, 200-400 mesh). The loading solution was prepared in 500 ml, of freshly boiled and cooled pure water (the pH was adjusted to 5). The resin was first eluted with freshly boiled and cooled water, then with formic acid.

General Procedure D:

The crude product synthesised by general procedure A or B was dissolved in 6N hydrochloric acid (5.0 mL). The mixture was stirred at 100° C. for 5 h, then cooled to room temperature. The solution was diluted with ethyl acetate (50 mL) and water (10 mL). The separated organic layer was extracted with of 1N hydrochloric acid (3×10 mL). The combined aqueous phases were concentrated under vacuum. The residue was purified using an anion exchange chromatography (Dowex AG 1-X4, AcO$^-$, 200-400 mesh). The loading solution was prepared in 500 mL of freshly boiled and cooled pure water (The pH was adjusted to 5). The resin was first eluted with freshly boiled and cooled water, then with dilute HCl.

General Procedure E (Preparation of Aryloxyacetic Acid Ethyl Ester):

To a solution of phenol (1 eq) in dry acetone, anhydrous potassium carbonate (1.3 eq) was added at room temperature. After 10 minutes, ethylbromoacetate (1.5 eq) was added and the mixture was refluxed and monitored by TLC until completion. After cooling, the solvent was removed under reduced pressure. The residue was added with water, then extracted with dichloromethane and washed with brine. The combined organic extracts were dried over magnesium sulfate, filtered and concentrated under vacuum. Ethanol or isopropanol was added and evaporated by azeotropic distillation in order to eliminate the ethylbromoacetate in excess. The solvent was evaporated to dryness, affording a residue which was chromatogaphed on a silica gel column (dichloromethane/ethyl acetate as eluent) to afford aryloxyacetic acid ethyl ester.

General Procedure F (Preparation of Alcohol):

NaBH$_4$ (1.1 eq) was added to a stirred and ice-bath cooled solution of aldehyde (1 eq) in THF and water (50/50). The reaction mixture was stirred for 45 minutes at 0° C. and, after distilling off the organic solvent, the aqueous residue was added with water (50 ml) and then extracted with dichloromethane (50 ml). The organic layer was washed with 10% Na$_2$CO$_3$ (20 ml) and brine (20 ml), then dried over Na$_2$SO$_4$, filtered, and evaporated in vacuo to dryness, affording a residue which was chromatographed on a silica gel column (dichloromethane/ethyl acetate as eluent).

General Procedure G (Preparation of Bromide):

PBr$_3$ (1 eq) was carefully added to a solution of alcohol (1 eq) in distilled dichloromethane at 0° C. under argon. The reaction mixture was stirred at 0° C. for 3 h and extracted with dichloromethane. The organic layer was washed with brine, dried over Na$_2$SO$_4$, filtered, and evaporated in vacuo to dryness without further purification.

Derivative 2

[((3S)-3-(N-Benzyloxycarbonyl)amino-3-methoxycarbonyl)propyl][(4-(carboxymethoxy)phenyl)hydroxymethyl]phosphinic Acid The compound was prepared according to general procedure B with H-phosphinic acid 1 (252 mg, 0.8 mmol) and 4-formylphenoxyacetic acid (317 mg, 1.8 mmol). 629 mg of crude product were obtained. $^{31}$P NMR (101 MHz, CD$_3$OD): δ 49.3.

[((3S)-3-Amino-3-carboxy)propyl][(4-(carboxymethoxy)phenyl)hydroxymethyl]phosphinic Acid (Derivative 2)

The previous compound was deprotected according to general procedure C. 150 mg of pure derivative 2 were obtained (54% yield, 2 steps). $^1$H NMR (250 MHz, D$_2$O): δ 1.71-194 (m, 2H), 1.98-2.00 (m, 2H), 3.95 (bs, 1H), 4.58 (s, 2H), 4.81 (bs, 1H), 6.85 (d, J=8.3 Hz, 2H), 7.25 (d, J=7.8 Hz, 2H). $^{31}$P NMR (101 MHz, D$_2$O): δ 55.4. $^{13}$C NMR (126 MHz, D$_2$O): δ 22.8 and 22.9 (2d, J=89 Hz), 24.1, 54.5 (d, J=15 Hz), 66.2, 73.0 (d, J=111 Hz), 110.0, 130.0, 131.3, 158.5, 172.8, 174.7. HPLC-MS: $t_R$=6.05 min. HPLC (Crownpak, T=5.0° C., detection λ=210/254 nm): $t_R$=18.4 min.

Derivative 3

[((3S)-3-(N-Benzyloxycarbonyl)amino-3-methoxycarbonyl)propyl][(3-methoxy-4-(methoxy carbonyl)methoxyphenyl)hydroxymethyl]phosphinic Acid)

The compound was prepared according to general procedure B with H-phosphinic acid 1 (292 mg, 0.9 mmol) and methyl 4-formyl-2-methoxyphenoxyacetate (457 mg, 2.0 mmol). 863 mg of crude product were obtained. $^{31}$P NMR (101 MHz, CD$_3$OD): δ 47.4.

[((3S)-3-Amino-3-carboxy)propyl][(3-methoxy-4-(carboxymethoxy)phenyl)hydroxymethyl]phosphinic Acid (Derivative 3)

The previous compound was deprotected according to general procedure D. The pure compound was obtained with a purification on anion exchange resin on 95 mg of crude product on a 14×1 cm column. The desired product was eluted with a 1.0×10$^{-2}$ N hydrochloric acid aqueous solution. 61 mg of pure derivative 3 were obtained (18% yield, 2 steps). $^1$H NMR (500 MHz, D$_2$O): δ 1.73-1.90 (m, 2H), 2.04-2.11 (m, 2H), 3.86 (s, 3H), 4.03 (q, J=6.0 Hz, 1H), 4.76 (s, 2H), 4.87 (d, J=8.5 Hz, 1H), 6.93 (d, J=8.5 Hz, 1H), 6.97 (d, J=8.5 Hz, 1H), 7.11 (s, 1H). $^{31}$P NMR (101 MHz, D$_2$O): δ 56.2. $^{13}$C NMR (126 MHz, D$_2$O): δ 22.7 (2d, J=89 Hz), 24.0, 54.4 (d, J=15 Hz), 57.2, 66.8, 73.0 (d, J=111 Hz), 112.6, 114.6, 121.2, 131.9, 147.7, 149.8, 172.6, 174.3. MS (ESI): m/z 376.0 (M−1). HPLC (Crownpak, T=10.0° C., detection λ=210/254 nm): $t_R$=15.4 min. HPLC (RP Polar, detection λ=230/270 nm): $t_R$=10.0 min.

Derivative 4

[((3S)-3-(N-Benzyloxycarbonyl)amino-3-methoxycarbonyl)propyl][(3,5-dimethoxy-4-(carboxy methoxy)phenyl)hydroxymethyl]phosphinic Acid)

The compound was prepared according to general procedure B with H-phosphinic acid (292 mg, 0.9 mmol) and 4-formyl-2,6-dimethoxyphenoxyacetic acid (250 mg, 1.0 mmol). $^{31}$P NMR (101 MHz, CD$_3$OD): δ 47.8.

[((3S)-3-Amino-3-carboxy)propyl][3,5-dimethoxy-4-(carboxymethoxy)phenyl)hydroxymethyl]phosphinic Acid (Derivative 4)

The previous compound was deprotected according to general procedure D. The pure compound was obtained with a purification on anion exchange resin on 300 mg of crude product on a 13×2 cm column. The desired product was eluted with a 1.5×10$^{-2}$ N hydrochloric acid aqueous solution. 155 mg of pure derivative 4 were obtained (42% yield, 2 steps). $^1$H NMR (500 MHz, D$_2$O): δ 1.85-1.96 (m, 2H), 2.06-2.11 (m, 2H), 3.81 (2s, 6H), 4.03 (m, 1H), 4.59 (m, 2H), 4.95 (d, J=8.5 Hz, 1H), 6.77 (s, 2H). $^{31}$P NMR (101 MHz, D$_2$O): δ 57.6. $^{13}$C NMR (126 MHz, D$_2$O): δ 22.8 (d, J=89 Hz), 24.0, 54.4 (d, J=15 Hz), 57.6, 70.8, 73.2 (d, J=110 Hz), 105.9, 134.5, 136.4, 153.2, 172.5, 174.8. MS (ESI): m/z 405.9 (M−1). HPLC (Crownpak, T=10.0° C., detection λ=210/254 nm): $t_R$=22.7 and 25.0 min. HPLC (RP Polar, detection λ=230/270 nm): $t_R$=14.7 min.

Derivative 5

Ethyl 4-formyl-2-methoxy-6-nitrophenoxyacetate

To a solution of 5-nitrovanilline (591 mg, 3.0 mmol) in DMF (9.0 mL) was added cesium carbonate (2.00 g, 6.16 mmol), followed by ethyl bromoacetate (3.33 mL, 30 mmol). The red mixture was left under stirring at 110° C. until it became yellow, and then for further 3 minutes. After evaporation of DMF under reduced pressure, 22 mL of water were added and the mixture was extracted with dichloromethane (60 mL). The organic phase was washed with brine (15 mL), dried over magnesium sulfate and concentrated under vacuum. The residue was purified by column chromatography over silica gel (eluent: dichloromethane) to give 625 mg of a solid (74% yield). $^1$H NMR (250 MHz, CDCl$_3$): δ 1.30 (t, J=7.2 Hz, 3H), 4.01 (s, 3H), 4.27 (q, J=7.2 Hz, 2H), 4.91 (s, 2H), 7.65 (s, 1H), 7.90 (s, 1H), 9.95 (s, 1H). $^{13}$C NMR (63 MHz, CDCl$_3$): δ 14.6, 57.2, 62.0, 70.0, 113.9, 120.4, 132.0, 145.2, 145.9, 154.2, 168.5, 189.3.

[((3S)-3-(N-Benzyloxycarbonyl)amino-3-methoxycarbonyl)propyl][(3-methoxy-5-nitro-4-(ethoxycarbonyl)methoxyphenyl)hydroxymethyl]phosphinic Acid The compound was prepared according to general procedure A with H-phosphinic acid 1 (243 mg, 0.77 mmol) and ethyl 4-formyl-2-methoxy-6-nitrophenoxyacetate (481 mg, 1.7 mmol). 169 mg of crude product were obtained. $^{31}$P NMR (101 MHz, CD$_3$COCD$_3$): δ 44.8.

[((3S)-3-Amino-3-carboxy)propyl][(3-methoxy-5-nitro-4-(carboxymethoxy)phenyl)hydroxymethyl]phosphinic Acid (Derivative 5). The previous compound was deprotected according to general procedure C. 42.4 mg of pure product derivative 5 were obtained (13% yield, 2 steps). $^1$H NMR (250 MHz, D$_2$O): δ 1.63-1.90 (m, 2H), 1.97-2.17 (m, 2H), 3.84 (s, 3H), 4.03 (m, 1H), 4.72 (s, 2H), 4.90 (d, J=9.5 Hz, 1H), 7.31 (s, 1H), 7.43 (s, 1H). $^{31}$P NMR (101 MHz, D$_2$O): δ 52.1. $^{13}$C NMR (126 MHz, D$_2$O): δ 23.1 and 23.2 (2d, J=89 Hz), 24.2, 54.6 (d, J=14 Hz), 71.2, 72.9 (d, J=108 Hz), 115.8, 117.5, 136.3, 140.9, 144.9, 154.3, 172.8, 174.3. MS (ESI): m/z 423.1 (M+1), 421.0 (M−1). HPLC-MS (Method A): $t_R$=9.51 min.

Derivative 6

Ethyl 2-(2-fluoro-4-formyl-6-methoxyphenoxy)acetate

To a solution of 3-fluoro-4-hydroxy-5-methoxybenzaldehyde (302 mg, 1.78 mmol) in acetone (20 mL) was added cesium carbonate (765 mg, 2.35 mmol), followed by ethyl bromoacetate (0.30 mL, 2.7 mmol). The mixture was refluxed in acetone under stirring for 1 hour. After evaporation of acetone under reduced pressure, 100 mL of water were added and the mixture was extracted with dichloromethane (200 mL). The organic phase was washed with brine (100 mL), dried over magnesium sulfate and concentrated under vacuum. The residue was purified by column chromatography over silica gel (eluent: dichloromethane) to give 361 mg of an oil (79% yield). $^1$H NMR (500 MHz, CD$_3$COCD$_3$): δ 1.25 (t, J=7.2 Hz, 3H), 3.98 (s, 3H), 4.20 (q, J=7.2 Hz, 2H), 4.89 (t, J=1.6 Hz 2H), 7.34 (dd, J=10.3 Hz, 1.6 Hz, 1H), 7.41 (s, 1H), 9.88 (d, J=1.5 Hz, 1H). $^{13}$C NMR (126 MHz, CD$_3$COCD$_3$): δ 15.0, 57.6, 62.1, 70.3 (d, J=1.9 Hz), 110.0, 111.8 (d, J=20.6 Hz), 133.1 (d, J=7.2 Hz), 141.8, (d, J=12.7 Hz), 154.8 (d, J=4.5 Hz), 155.0 d, J=46.1 Hz) 169.7, 191.3.

[((3S)-3-(N-Benzyloxycarbonyl)amino-3-methoxy-carbonyl)propyl][(3-fluoro-5-methoxy-4-(ethoxycarbonyl)methoxyphenyl)hydroxymethyl]phosphinic Acid The compound was prepared according to general procedure A with H-phosphinic acid (465 mg, 1.48 mmol) and ethyl 2-(2-fluoro-4-formyl-6-methoxyphenoxy)acetate (361 mg, 1.41 mmol). 1.3 g of crude product were obtained. $^{31}$P NMR (101 MHz, CD$_3$OD): δ 47.6. MS (ESI): m/z 570.1 (M−1)

[((3S)-3-Amino-3-carboxy)propyl][(3-fluoro-5-methoxy-4-(carboxymethoxy)phenyl hydroxymethyl]phosphinic Acid (Derivative 6)

The previous compound was deprotected according to general procedure C. 115.0 mg of pure derivative 6 were obtained (21% yield, 2 steps). $^1$H NMR (500 MHz, D$_2$O): δ 1.80-1.80 (m, 2H), 1.99-2.08 (m, 2H), 3.77 (s, 3H), 3.95 (m, 1H), 4.60 (s, 2H), 4.74 (d, J=9.7 Hz, 1H), 6.77 (d, J=11.3 Hz, 1H), 6.83 (s, 1H). $^{31}$P NMR (202 MHz, D$_2$O): δ 40.3. $^{13}$C NMR (126 MHz, D$_2$O): δ 23.0 and 23.8 (dd, J=89.4; 7.7 Hz), 24.4, 54.8 (d, J=14.1 Hz), 57.7, 71.0, 73.5 (d, J=107.7 Hz), 108.5, 108.8 (d, J=20.9 Hz), 135.0 (d, J=12.8 Hz), 135.7 (d, J=8.5 Hz), 153.7, 156.0 (d, J=244 Hz), 173.1, 174.6. MS (ESI): m/z 396.0 (M+1). HPLC-MS (Method A): t$_R$=7.91 min.

Derivative 7

Ethyl 2-(2-chloro-4-formyl-6-methoxyphenoxy)acetate

To a solution of 5-chlorovanilline (505 mg, 2.7 mmol) in acetone (25 mL) was added cesium carbonate (1.16 g, 3.56 mmol), followed by ethyl bromoacetate (0.45 mL, 4.05 mmol). The mixture was refluxed in acetone under stirring for 1 hour. After evaporation of acetone under reduced pressure, 100 mL of water were added and the mixture was extracted with dichloromethane (200 mL). The organic phase was washed with brine (100 mL), dried over magnesium sulfate and concentrated under vacuum. The residue was purified by column chromatography over silica gel (eluent: dichloromethane) to give 330 mg of an oil (45% yield). $^1$H NMR (250 MHz, CD$_3$COCD$_3$): δ 1.27 (t, J=7.2 Hz, 3H), 3.98 (s, 3H), 4.22 (q, J=7.2 Hz, 2H), 4.87 (s, 2H), 7.50 (s, 1H), 7.58 (s, 1H), 9.90 (s, 1H). $^{13}$C NMR (126 MHz, CD$_3$COCD$_3$): δ 15.1, 57.5, 62.1, 70.5, 112.3, 125.8, 128.9, 134.0, 149.7, 154.5, 169.5, 191.2.

[((3S)-3-(N-Benzyloxycarbonyl)amino-3-methoxy-carbonyl)propyl][(3-chloro-5-methoxy-4-(ethoxycarbonyl)methoxyphenyl)hydroxymethyl]phosphinic Acid The compound was prepared according to general procedure A with H-phosphinic acid (398 mg, 1.3 mmol) and Ethyl 2-(2-chloro-4-formyl-6-methoxyphenoxy)acetate (330 mg, 1.2 mmol). 819 mg of crude product were obtained. $^{31}$P NMR (101 MHz, CD$_3$COCD$_3$): δ 48.2. MS (ESI): m/z 587.8 (M+1), 585.9 (M−1)

[((3S)-3-Amino-3-carboxy)propyl][(3-chloro-5-methoxy-4-(carboxymethoxy)phenyl hydroxymethyl]phosphinic Acid (Derivative 7)

The previous compound was deprotected according to general procedure C. 120.0 mg of pure derivative 7 were obtained (26% yield, 2 steps). $^1$H NMR (500 MHz, D$_2$O): δ 1.78-1.87 (m, 2H), 2.05-2.11 (m, 2H), 3.78 (s, 3H), 4.03 (m, 1H), 4.57 (s, 2H), 4.85 (d, J=9.2 Hz, 1H), 6.98 (s, 1H), 7.02 (s, 1H). $^{31}$P NMR (202 MHz, D$_2$O): δ 43.6. $^{13}$C NMR (126 MHz, D$_2$O): δ 22.5 and 23.3 (dd, J=88.3; 6.6 Hz), 24.1, 54.5 (d, J=14.6 Hz), 57.6, 70.6, 72.9 (d, J=108.9 Hz), 111.8, 121.5, 128.4, 136.0, 143.5, 154.0, 172.7, 174.4. MS (ESI): m/z 410.0 (M−1). HPLC-MS (Method A): t$_R$=9.00 min.

Derivative 8

Ethyl 2-(2-iodo-4-formyl-6-methoxyphenoxy)acetate

To a solution of 5-iodovanilline (502 mg, 1.8 mmol) in acetone (25 mL) was added cesium carbonate (766 mg, 2.35 mmol), followed by ethyl bromoacetate (0.30 mL, 2.7 mmol). The mixture was refluxed in acetone under stirring for 1 hour. After evaporation of acetone under reduced pressure, 100 mL of water were added and the mixture was extracted with dichloromethane (200 mL). The organic phase was washed with brine (100 mL), dried over magnesium sulfate and concentrated under vacuum. The residue was purified by column chromatography over silica gel (eluent: dichloromethane) to give 320 mg of a yellow solid (49% yield). $^1$H NMR (250 MHz, CD$_3$COCD$_3$): δ 1.28 (t, J=7.2 Hz, 3H), 3.97 (s, 3H), 4.23 (q, J=7.2 Hz, 2H), 4.85 (s, 2H), 7.55 (s, 1H), 7.95 (s, 1H), 9.89 (s, 1H). $^{13}$C NMR (126 MHz, CD$_3$COCD$_3$): δ 15.2, 57.4, 62.1, 70.5, 92.4, 113.9, 135.1, 135.5, 153.1 (2C), 169.4, 169.5, 191.0.

[((3S)-3-(N-Benzyloxycarbonyl)amino-3-methoxy-carbonyl)propyl][(3-iodo-5-methoxy-4-(ethoxycarbonyl)methoxyphenyl)hydroxymethyl]phosphinic Acid The compound was prepared according to general procedure A with H-phosphinic acid (289 mg, 0.92 mmol) and Ethyl 2-(2-iodo-4-formyl-6-methoxyphenoxy)acetate (320 mg, 0.88 mmol). 516 mg of crude product were obtained. $^{31}$P NMR (101 MHz, CD$_3$COCD$_3$): δ 48.1. MS (ESI): m/z 677.9 (M−1)

[((3S)-3-Amino-3-carboxy)propyl][(3-iodo-5-methoxy-4-(carboxymethoxy)phenyl hydroxymethyl] phosphinic Acid (Derivative 8)

The previous compound was deprotected according to general procedure C. 90.0 mg of pure derivative 8 were obtained (20% yield, 2 steps). $^1$H NMR (500 MHz, D$_2$O): δ 1.73-1.77 (m, 2H), 2.05-2.08 (m, 2H), 3.81 (s, 3H), 4.00 (m, 1H), 4.56 (s, 2H), 4.78 (d, J=9.4 Hz, 1H), 7.07 (s, 1H), 7.40 (s, 1H). $^{31}$P NMR (202 MHz, D$_2$O): δ 40.4. $^{13}$C NMR (126 MHz, D$_2$O): δ 23.1 and 23.9 (dd, J=89.2; 10.4 Hz), 24.5, 54.9 (d, J=13.9 Hz), 57.5, 70.6, 73.1 (d, J=108.0 Hz), 92.2, 113.6, 130.1, 138.2, 147.1, 152.9, 173.2, 174.5. MS (ESI): m/z 501.9 (M−1). HPLC-MS (Method A): t$_R$=12.15 min.

Derivative 9 ethyl 2-(2,6-dichloro-4-formylphenoxy)acetate

To a solution of 3,5-dichloro-4-hydroxybenzaldehyde (302 mg, 1.6 mmol) in acetone (15 mL) was added cesium carbonate (700 mg, 2.15 mmol), followed by ethyl bromoacetate (0.27 mL, 2.43 mmol). The mixture was refluxed in acetone under stirring for 1 hour. After evaporation of acetone under reduced pressure, 100 ml of water were added and the mixture was extracted with dichloromethane (200 mL). The organic phase was washed with brine (100 mL), dried over magnesium sulfate and concentrated under vacuum. The residue was purified by column chromatography over silica gel (eluent: dichloromethane) to give 264 mg of an oil (59% yield). $^1$H NMR (500 MHz, CDCl$_3$): δ 1.29 (t, J=7.2 Hz, 3H), 4.26 (q, J=7.2 Hz, 2H), 4.85 (s, 2H), 7.96 (s, 2H), 9.98 (s, 1H). $^{13}$C NMR (126 MHz, CD$_3$COCD$_3$): δ 15.0, 62.3, 70.8, 131.2, 131.4, 135.4, 156.4, 168.4, 190.5.

[((3S)-3-(N-Benzyloxycarbonyl)amino-3-methoxycarbonyl)propyl][(3,5-dichloro-4-(ethoxycarbonyl)methoxyphenyl)hydroxymethyl]phosphinic Acid The compound was prepared according to general procedure A with H-phosphinic acid (315 mg, 1.0 mmol) and ethyl 2-(2,6-dichloro-4-formylphenoxy)acetate (264 mg, 0.956 mmol). 553 mg of crude product were obtained. $^{31}$P NMR (101 MHz, CD$_3$COCD$_3$): δ 47.3 MS (ESI): m/z 591.0 (M−1)

[((3S)-3-Amino-3-carboxy)propyl][(3,5-dichloro-4-(carboxymethoxy)phenyl hydroxy methyl]phosphinic Acid (Derivative 9)

The previous compound was deprotected according to general procedure C. 102.0 mg of pure derivative 9 were obtained (26% yield, 2 steps). $^1$H NMR (250 MHz, D$_2$O): δ 1.69-1.81 (m, 2H), 2.02-2.12 (m, 2H), 4.03 (m, 1H), 4.69 (s, 2H), 4.78 (d, J=9.6 Hz, 1H), 7.41 (s, 1H). $^{31}$P NMR (101 MHz, D$_2$O): δ 39.3. $^{13}$C NMR (126 MHz, D$_2$O): δ 23.6 and 24.4 (dd, J=78.7; 13.8 Hz), 24.8, 55.5, 70.8, 73.2 (d, J=117.4 Hz), 128.7, 129.8, 138.6, 150.1, 174.3, 174.4 MS (ESI): m/z 413.9 (M−1). HPLC MS (Method A): t$_R$=11.34 min.

Derivative 10 ethyl 2-(4-formyl-2,6-dimethylphenoxy)acetate

To a solution of 4-hydroxy-3,5-dimethylbenzaldehyde (500 mg, 3.33 mmol) in acetone (20 mL) was added cesium carbonate (1.41 g, 4.33 mmol), followed by ethyl bromoacetate (0.555 mL, 5 mmol). The mixture was refluxed in acetone under stirring for 1 hour. After evaporation of acetone under reduced pressure, 100 mL of water were added and the mixture was extracted with dichloromethane (200 mL). The organic phase was washed with brine (100 mL), dried over magnesium sulfate and concentrated under vacuum. The residue was purified by column chromatography over silica gel (eluent: dichloromethane) to give 580 mg of an oil (74% yield). $^1$H NMR (250 MHz, CDCl$_3$): δ 1.25 (t, J=6.9 Hz, 3H), 4.27 (s, 6H), 4.21 (q, J=6.9 Hz, 2H), 4.38 (s, 2H), 7.44 (s, 2H), 9.77 (s, 1H). $^{13}$C NMR (126 MHz, CDCl$_3$): δ 15.2, 17.4, 62.2, 70.1, 131.6, 132.8, 133.8, 161.7, 169.5, 192.1.

[((3S)-3-(N-Benzyloxycarbonyl)amino-3-methoxycarbonyl)propyl][(3,5-dimethyl-4-(ethoxycarbonyl)methoxyphenyl)hydroxymethyl]phosphinic Acid The compound was prepared according to general procedure A with H-phosphinic acid (809 mg, 2.57 mmol) and ethyl 2-(4-formyl-2,6-dimethylphenoxy)acetate (580 mg, 2.46 mmol). 1.4 g of crude product were obtained. $^{31}$P NMR (101 MHz, CDCl$_{33}$): δ 50.1 MS (ESI): m/z 550.1 (M−1)

[((3S)-3-Amino-3-carboxy)propyl][(3,5-dimethyl-4-(carboxymethoxy)phenyl hydroxy methyl]phosphinic Acid (Derivative 10)

The previous compound was deprotected according to general procedure C. 238.0 mg of pure derivative 10 were obtained (26% yield, 2 steps). $^1$H NMR (500 MHz, D$_2$O): δ 1.70-1.86 (m, 2H), 1.98-2.06 (m, 2H) 2.16 (s, 6H), 3.97 (m, 1H), 4.41 (s, 2H), 4.77 (d, J=8.7 Hz, 1H), 7.03 (s, 2H). $^{31}$P NMR (202 MHz, D$_2$O): δ 43.3. $^{13}$C NMR (126 MHz, D$_2$O): δ 16.8, 22.6 and 23.3 (dd, J=88.5; 8.7 Hz), 24.2, 54.6 (d, J=14.5 Hz), 69.9, 73.2 (d, J=109.3 Hz), 128.9, 132.6, 134.5, 155.4, 172.9, 174.6 MS (ESI): m/z 374.1 (M−1), 376.0 (M+1). HPLC-MS (Method A): t$_R$=8.33 min.

Derivative 11

[((3S)-3-(N-Benzyloxycarbonyl)amino-3-methoxycarbonyl)propyl][(4-((E)-2-carboxyethenyl)phenyl)hydroxymethyl]phosphinic Acid)

The compound was prepared according to general procedure B with H-phosphinic acid (315 mg, 1.0 mmol) and (E)-4-formyl-phenylacrylic acid (388 mg, 2.2 mmol). The reaction was stirred for 48 h to achieve complete conversion. $^{31}$P NMR (101 MHz, CD$_3$OD): δ 48.7.

[((3S)-3-Amino-3-carboxy)propyl][(4-((E)-2-carboxyethenyl)phenyl)hydroxymethyl]phosphinic Acid (Derivative 11)

The previous compound was deprotected according to general procedure C. After the cation exchange resin, 355 mg of compound were obtained. A second purification on an anion exchange resin (AG 1-X4, 200-400 Mesh, 18×2.5 cm, AcO$^-$) was necessary to obtain a pure compound. The crude compound was diluted in 500 mL of pure and freshly boiled and cooled water, and the pH was brought to 9 (with a freshly prepared 1N sodium hydroxide aqueous solution). The resin was eluted with formic acid (1N to 5N) and the desired compound was eluted with 3N formic acid. 158 mg of pure derivative 11 were obtained (46% yield, 2 steps). $^1$H NMR (500 MHz, D$_2$O): δ 1.76-1.87 (m, 2H), 2.05-2.16 (m, 2H), 4.05 (t, J=6.0 Hz, 1H), 4.94 (d, J=10.0 Hz, 1H), 6.47 and 6.48 (2d, J=16.0 Hz, 1H), 7.45 (d, J=7.5 Hz, 2H), 7.61 (d, J=5.5 Hz, 2H), 7.67 and 7.68 (2d, J=16.0 Hz, 1H). $^{31}$P NMR (101 MHz, D$_2$O): δ 53.0. $^{13}$C NMR (126 MHz, D$_2$O): δ 23.2 (d, J=86 Hz), 24.4, 54.8, 74.0 (d, J=106 Hz), 118.9, 128.9, 129.9, 135.1, 141.3, 147.5, 172.4, 173.0. HPLC-MS: t$_R$=7.49 min.

Derivative 12

Ethyl 3-(4-formyl)-phenylpropanoate the compound was prepared according to a previously described procedure (a) Battistuzzi, G.; Cacchi, S.; Fabrizi, G.; Bernini, R. 3-Arylpropanoate esters through the palladium-catalyzed reaction of aryl halides with acrolein diethyl acetal. *Synlett* 2003, 8, 1133-1136. b) Giannini, G.; Marzi, M.; Pezzi, R.; Brunetti, T.; Battistuzzi, G.; Di Marzo, M.; Cabri, W.; Vesci, L.; Pisano, C. N-hydroxy-(4-oxime)-cinnamide: a versatile scaffold for the synthesis of novel histone deacetilase (HDAC) inhibitors. *Bioorg. Med. Chem. Lett.*

2009, 19, 2346-2349). To a solution of 4-bromobenzaldehyde (740 mg, 4.0 mmol), acrolein diethylacetal (1.83 mL, 12 mmol), tetra-n-butylammonium chloride (1.11 g, 4.0 mmol), tributylamine (1.91 mL, 8.0 mmol) in 16 mL of DMF, palladium(II) acetate (27 mg, 0.12 mmol) was added. The mixture was warmed at 90° C. and stirred overnight. After cooling, the reaction mixture was diluted with 2N HCl (60 mL) and extracted with diethyl ether (60 mL×3). The organic layer was dried over magnesium sulfate and concentrated under reduced pressure. The residue was purified by column chromatography over silica gel (eluent: 5-15% EtOAc/cyclohexane) to give 538 mg of a yellow oil (65% yield). $^1$H NMR (250 MHz, CDCl$_3$): δ 1.25 (t, J=7.0 Hz, 3H), 2.68 (d, J=7.5 Hz, 2H) 3.06 (d, J=7.5 Hz, 2H), 4.14 (q, J=7.0 Hz, 2H), 7.40 (d, J=8.2 Hz, 2H), 7.83 (d, J=8.2 Hz, 2H), 10.00 (s, 1H). $^{13}$C NMR (63 MHz, CDCl$_3$): δ 14.6, 31.5, 35.7, 61.1, 129.4, 130.4, 135.2, 148.3, 172.8, 192.4.

[((3S)-3-(N-Benzyloxycarbonyl)amino-3-methoxycarbonyl)propyl][(4-(ethoxycarbonyl ethyl)phenyl) hydroxymethyl]phosphinic Acid The compound was prepared according to general procedure A with H-phosphinic acid 1 (375 mg, 1.19 mmol) and ethyl 3-(4-formyl)-phenylpropanoate (540 mg, 2.62 mmol). 336 mg of crude product were obtained. $^{31}$P NMR (101 MHz, CD$_3$COCD$_3$): δ 45.6.

[((3S)-3-Amino-3-carboxy)propyl][(4-(carboxyethyl)phenyl)hydroxymethyl]phosphinic Acid (Derivative 12)

The previous compound was deprotected according to general procedure C. 152.6 mg of pure product derivative 12 were obtained (37% yield, 2 steps). $^1$H NMR (500 MHz, D$_2$O): δ 1.74-1.99 (m, 2H), 2.01-2.15 (m, 2H), 2.68 (t, J=7.3 Hz, 2H), 2.91 (t, J=7.3 Hz, 2H), 4.05 (m, 1H), 4.94 (d, J=9.0 Hz, 1H), 7.28 (d, J=8.0 Hz, 2H), 7.35 (d, J=8.0 Hz, 2H). $^{31}$P NMR (101 MHz, D$_2$O): δ 55.7. $^{13}$C NMR (126 MHz, D$_2$O): δ 22.7 and 22.8 (2d, J=89 Hz), 24.1, 31.4, 36.7, 54.5 (d, J=14 Hz), 73.5 (d, J=109 Hz), 128.7, 129.9, 135.8, 142.3, 172.7, 179.3. MS (ESI): m/z 346.0 (M+1), 344.0 (M−1). HPLC-MS (Method A): t$_R$=9.27 min.

Derivative 13

[((3S)-3-(N-Benzyloxycarbonyl)amino-3-methoxycarbonyl)propyl][(4-(2-hydroxyethoxy)phenyl)hydroxymethyl]phosphinic Acid The compound was prepared according to general procedure B with H-phosphinic acid 1 (304 mg, 1.0 mmol) and 4-(2-hydroxyethoxy)benzaldehyde (353 mg, 2.2 mmol). 773 mg of crude product were obtained. $^{31}$P NMR (101 MHz, CD$_3$OD): δ 49.2.

[((3S)-3-Amino-3-carboxy)propyl][(4-(2-hydroxyethoxy)phenyl)hydroxymethyl]phosphinic Acid (Derivative 13)

The previous compound was deprotected according to general procedure D. The purification on anion exchange column was performed with 73 mg of crude product on a 21×1 cm column. The desired product was eluted with a 2.5×10$^{-2}$ N hydrochloric acid aqueous solution. 49.0 mg of pure derivative 13 were obtained (15% yield, 2 steps). $^1$H NMR (500 MHz, D$_2$O): δ 1.78-1.87 (m, 2H), 2.06-2.09 (m, 2H), 3.87 (m, 2H), 4.03 (q, J=5.0 Hz, 1H), 4.11 (m, 2H), 4.88 (d, J=7.5 Hz, 1H), 7.00 (dd, J=2.5/8.0 Hz, 2H), 7.35 (dd, J=3.0/8.0 Hz, 2H). $^{31}$P NMR (101 MHz, D$_2$O): δ 55.1. $^{13}$C NMR (126 MHz, D$_2$O): δ 22.9 and 23.0 (2d, J=89 Hz), 24.2, 54.6 (d, J=15 Hz), 61.6, 70.8, 73.2 (d, J=111 Hz), 116.3, 130.0, 130.7, 159.6, 172.9. MS (ESI): m/z 332.0 (M−1). HPLC (Crownpak, T=10.0° C., detection λ=210/254 nm): t$_R$=9.9 min. HPLC (RP Polar, detection λ=230/270 nm): t$_R$=8.7 min.

Derivative 14 diisopropyl(4-formylphenoxy)methylphosphonate

To a solution of 4-hydroxybenzaldehyde (152 mg, 1.25 mmol) in DMF (20 mL) was added potassium carbonate (223 mg, 1.62 mmol), followed by diisopropyl bromomethylphosphonate (484 mg, 1.87 mmol). The mixture was heating in DMF at 90° C. under stirring for 17 hours. After evaporation of DMF under reduced pressure, 100 mL of water were added and the mixture was extracted with ethyl acetate (3*200 mL). The organic phase was washed with brine (100 mL), dried over magnesium sulfate and concentrated under vacuum. The residue was purified by column chromatography over silica gel (eluent: cyclohexane/ethyl acetate (5:5)) to give 98.2 mg of an oil (26% yield). $^1$H NMR (250 MHz, CDCl$_3$): δ 1.33 (t, J=6.0 Hz, 12H), 4.25 (d, J=10.2 Hz, 2H), 4.82 (q, J=6.0 Hz, 2H), 7.05 (d, J=8.7 Hz, 2H), 7.81 (d, J=8.7 Hz, 2H), 9.87 (s, 1H). $^{13}$C NMR (126 MHz, CDCl$_3$): δ 25.4 (dd, J=12.7; 3.4 Hz), 64.0 (d, J=171.0 Hz) 73.3 (d, J=6.2 Hz), 116.3, 132.2, 133.3, 164.8 (d, J=13.4 Hz), 192.0. $^{31}$P NMR (202 MHz, CDCl$_3$): δ 16.0

[((3S)-3-(N-Benzyloxycarbonyl)amino-3-methoxycarbonyl)propyl][(4-((diisopropoxyphosphoryl) methoxy)phenyl)hydroxymethyl]phosphinic Acid The compound was prepared according to general procedure A with H-phosphinic acid (68.8 mg, 0.22 mmol) and diisopropyl(4-formylphenoxy)methylphosphonate (98.2 mg, 0.327 mmol). 115 mg of crude product were obtained. $^{31}$P NMR (101 MHz, CD$_3$OD): δ 47.7; 18.2 MS (ESI): m/z 616.0 (M+1)

[((3S)-3-Amino-3-carboxy)propyl][(4-phosphonomethoxyphenyl)hydroxymethyl]phosphinic Acid (Derivative 14)

The previous compound was deprotected according to general procedure C. After the cation exchange resin, 52.1 mg of compound were obtained. A second purification on an anion exchange resin (AG 1-X4, 200-400 Mesh, 10.5×1.5 cm, AcO$^-$) was necessary to obtain a pure compound. The crude compound was diluted in 150 mL of pure and freshly boiled and cooled water, and the pH was brought to 9 (with a freshly prepared 1N sodium hydroxide aqueous solution). The resin was eluted with formic acid (1.8N to 3.5N) and the desired compound was eluted with 3N formic acid. 14.6 mg of pure derivative 14 were obtained (17% yield, 2 steps). $^1$H NMR (500 MHz, D$_2$O): δ 1.62-1.77 (m, 2H), 2.01-2.09 (m, 2H), 3.9 (m, 1H), 4.12 (d, J=9.2 Hz, 2H), 4.76 (d, J=7.6 Hz, 1H), 7.02 (d, J=7.0 Hz, 2H), 7.34 (d, J=7.0 Hz, 2H). $^{31}$P NMR (202 MHz, D$_2$O): δ 39.4; 14.7. $^{13}$C NMR (126 MHz, D$_2$O): δ 23.4 (dd, J=89.6; 16.4 Hz), 24.9, 55.6, 65.6 (d, J=158.3 Hz), 73.9 (d, J=109.3 Hz), 116.1, 129.8, 132.0, 160.0 (d, J=12.2 Hz), 174.1. HPLC-MS (Method A): t$_R$=5.14, (ESI): m/z 383.9 (M+1) m/z 382.0 (M−1)

Derivative 15

[((3S)-3-(N-Benzyloxycarbonyl)amino-3-methoxycarbonyl)propyl][(3-(ethoxycarbonyl) methoxyphenyl)hydroxymethyl]phosphinic Acid The compound was prepared according to general procedure B with H-phosphinic acid 1 (315 mg, 1.0 mmol) and ethyl 3-formylphenoxyacetate (458 mg, 2.2 mmol). The reaction had to be stirred for 48 h to achieve complete conversion. $^{31}$P NMR (101 MHz, CD$_3$OD): δ 57.8.

[((3S)-3-Amino-3-carboxy)propyl][(3-(carboxymethoxy)phenyl)hydroxymethyl]phosphinic Acid (Derivative 15)

The previous compound was deprotected according to general procedure C. 229 mg of pure product derivative 15 were obtained (66% yield, 2 steps). $^1$H NMR (500 MHz, D$_2$O): δ 1.79-1.93 (m, 2H), 2.05-2.12 (m, 2H), 4.05 (q, J=6.0 Hz, 1H), 4.94 (d, J=9.5 Hz, 1H), 6.92 (d, J=8.0 Hz, 1H), 6.99 (d, J=1.5 Hz, 1H), 7.05 (d, J=8.0 Hz, 1H), 7.33 (t, J=8.0 Hz, 1H). $^{31}$P NMR (101 MHz, D$_2$O): δ 56.6. $^{13}$C NMR (126 MHz, D$_2$O): δ 22.6 (2d, J=89 Hz), 23.9, 54.4 (d, J=15 Hz), 66.2, 73.2 (d, J=109 Hz), 114.5, 115.8, 122.0, 131.4, 139.6, 158.6, 172.5, 174.6. MS (ESI): m/z 346.1 (M−1). HPLC (Crownpak, T=10.0° C., detection λ=210/254 nm): $t_R$=20.6 and 22.9 min.

[((3S)-3-Ammonium-3-carboxy)propyl][(3-(carboxymethoxy)phenyl)hydroxymethyl]phosphinic Acid Hydrochloride (Derivative 16-diaI and Derivative 17-diaII)

The diastereoisomers of derivative 15 were separated by HPLC using the preparative Crownpak column at 4.0° C. with a 1.0 mL·min$^{-1}$ flow, a 2 mL injection loop, and a dual UV detection at 210 and 254 nm. 21 injections were performed in order to obtain enough product for pharmacological tests. Each injection was prepared with 2.5 mg of derivative 15 in 1.5 mL of pH 2.0 hydrochloric acid. The diastereoisomer with the shortest retention time was named -I and the other one -II. 18 mg of pure dia-I derivative 16 and 22 mg of pure dia-II derivative 17 were obtained. Derivative 16-diaI: $^1$H NMR (500 MHz, D$_2$O): δ 1.78 (m, 2H), 2.08 (m, 2H), 4.03 (bs, 1H), 4.76 (s, 2H), 4.88 (d, J=9.5 Hz, 1H), 6.93 (d, J=7.5 Hz, 1H), 7.02 (bs, 1H), 7.08 (d, J=7.0 Hz, 1H), 7.35 (dd, J=7.5/8.0 Hz, 1H). $^{13}$C NMR (126 MHz, D$_2$O): δ 22.9 (d, J=88 Hz), 24.1, 54.6 (d, J=14 Hz), 66.4, 73.6 (d, J=108 Hz), 114.5, 115.7, 122.1, 131.4, 140.2, 158.6, 172.8, 174.8. MS (ESI): m/z 346.1 (M−1). HPLC (Crownpak, T=4.0° C., detection λ=210/254 nm): $t_R$=21.3 min. $[α]_D^{20}$: +3.3 (H$_2$O, c 0.9). Derivative 17-diaII: $^1$H NMR (500 MHz, D$_2$O): δ 1.73-1.88 (m, 2H), 2.08-2.13 (m, 2H), 4.03 (bs, 1H), 4.76 (s, 2H), 4.91 (d, J=7.5 Hz, 1H), 6.93 (d, J=6.0 Hz, 1H), 7.01 (bs, 1H), 7.07 (d, J=4.0 Hz, 1H), 7.35 (bs, 1H). $^{13}$C NMR (126 MHz, D$_2$O): δ 22.8 (d, J=89 Hz), 24.0, 54.6, 66.3, 73.9, 114.5, 115.8, 122.1, 131.4, 139.9, 158.6, 172.7, 174.7. MS (ESI): m/z 346.1 (M−1). HPLC (Crownpak, T=4.0° C., detection λ=210/254 nm): $t_R$=23.9 min. $[α]_D^{20}$: +17.5 (H$_2$O, c 1.1).

Derivative 18

3,4-Bis(ethoxycarbonylmethoxy)benzaldehyde

To a suspension of 3,4-dihydroxybenzaldehyde (691 mg, 5.0 mmol) in dimethylformamide (10.0 mL) was added potassium carbonate (2.76 g, 4 eq). This mixture was stirred for 30 min at room temperature then cooled at 0° C. Ethylbromoacetate (1.66 mL, 15.0 mmol) was added, and the mixture was allowed to warm at room temperature and stirred for 19 h. The mixture was then diluted in water (50 mL) and extracted with ethyl acetate (2×150 mL). The combined organic phases were washed with brine (20 mL), dried with magnesium sulfate, filtered and concentrated under vacuum. A brown oil was obtained and filtered on a silica gel layer, using cyclohexane/ethyl acetate (1:1, 250 mL). The filtrates containing the desired product were concentrated under vacuum. This orange oil, still containing traces of dimethylformamide, was directly engaged in the following step.

A sample of crude 3,4-bis(ethoxycarbonylmethoxy)benzaldehyde was purified by silica gel chromatography (eluant cyclohexane/ethyl acetate in gradient from 3:1 to 6:4) to afford pure compound that was used for the NMR characterization. $^1$H NMR (500 MHz, CDCl$_3$): δ 1.23 (2t, J=7.5 Hz, 6H), 4.20 (q, J=7.5 Hz, 4H), 4.72 and 4.75 (2s, 4H), 6.89 (d, J=8.0 Hz, 1H), 7.33 (d, J=1.5 Hz, 1H), 7.41 (dd, J=1.5/8.0 Hz, 1H), 9.77 (s, 1H). $^{13}$C NMR (126 MHz, CDCl$_3$): δ 15.5, 62.8 and 62.9, 67.5 and 67.6, 114.5 and 115.0, 128.1, 132.4, 149.6, 154.4, 169.4 and 169.7, 191.8. TLC: $R_f$=0.5 (cyclohexane/ethyl acetate 1:1).

[((3S)-3-(N-Benzyloxycarbonyl)amino-3-methoxycarbonyl)propyl][(3,4-di(ethoxycarbonyl methoxy)phenyl)hydroxymethyl]phosphinic Acid This compound was synthesized according to general procedure B with 1 (282 mg, 0.9 mmol) and the previously synthesized 3,4-bis(ethoxycarbonylmethoxy)benzaldehyde. $^{31}$P NMR (101 MHz, CD$_3$OD): δ 48.9.

[((3S)-3-Amino-3-carboxy)propyl][(3,4-di(carboxymethoxy)phenyl)hydroxymethyl]phosphinic Acid (Derivative 18)

The deprotection was achieved according to general procedure C. Two cation exchange columns were necessary to obtain the pure compound. 51 mg of a pure fraction of derivative 18 were obtained (13% yield, 2 steps). $^1$H NMR (500 MHz, D$_2$O): δ 1.73-1.86 (m, 2H), 2.03-2.09 (m, 2H), 4.03 (q, J=6.0 Hz, 1H), 4.79 and 4.80 (2s, 4H), 4.85 (d, J=9.0 Hz, 1H), 6.98 (d, J=8.5 Hz, 1H), 7.0-7.04 (m, 2H). $^{31}$P NMR (101 MHz, D$_2$O): δ 53.0. $^{13}$C NMR (126 MHz, D$_2$O): δ 23.0 and 23.1 (2d, J=89 Hz), 24.3, 54.7 (d, J=15 Hz), 67.1, 73.4 (d, J=109 Hz), 114.2, 115.5, 122.6, 132.7, 148.0 and 148.1, 173.0, 174.6. HPLC-MS (Method A): $t_R$=6.25 (ESI): m/z 422.0 (M+1) m/z 420.0 (M−1).

Ethyl 2-(2-chloro-4-formyl-6-methoxyphenoxy)acetate

The compound was prepared according to general procedure E with 5-chlorovanillin (2.7 mmol) in dry acetone (25 ml), anhydrous K$_2$CO$_3$ (3.5 mmol), and ethylbromoacetate (4.05 mmol) at reflux for 1 h30. Ethanol was added and evaporated by azeotropic distillation with ethylbromoacetate. 957 mg of crude product were obtained and purified by silica gel chromatography (eluent dichloromethane). 330 mg of purified compound were obtained (45% yield). $^1$H NMR (250 MHz, CD$_3$COCD$_3$): δ 1.27 (t, J=7.2 Hz, 3H), 3.98 (s, 3H), 4.22 (q, J=7.2 Hz, 2H), 4.87 (s, 2H), 7.50 (s, 1H), 7.58 (s, 1H), 9.90 (s, 1H) $^{13}$C NMR (126 MHz, CD$_3$COCD$_3$): δ 15.1, 57.5, 62.1, 70.5, 112.3, 125.8, 128.9, 134.0, 149.7, 154.5, 169.5, 191.2. MS (ESI): m/z 272.9 and 274.9 [M+H]$^+$.

Ethyl 2-(2 iodo-4-formyl-6-methoxyphenoxy)acetate

The compound was prepared according to general procedure E with 5-iodovanillin (1.8 mmol) in dry acetone (25 ml), anhydrous $K_2CO_3$ (2.4 mmol), and ethylbromoacetate (2.7 mmol) at reflux for 1 h15. Ethanol was added and evaporated by azeotropic distillation with ethylbromoacetate. 673 mg of crude product were obtained and purified by silica gel chromatography (eluent dichloromethane). 320 mg of purified compound were obtained (49% yield). $^1$H NMR (250 MHz, $CD_3COCD_3$): δ 1.28 (t, J=7.2 Hz, 3H), 3.97 (s, 3H), 4.23 (q, J=7.2 Hz, 2H), 4.85 (s, 2H), 7.55 (s, 1H), 7.95 (s, 1H), 9.90 (s, 1H) $^{13}$C NMR (126 MHz, $CD_3COCD_3$): δ 15.2, 57.4, 62.1, 70.5, 92.4, 113.9, 135.1, 135.5, 153.1, 169.4, 191.1. MS (ESI): m/z 364.9 $[M+H]^+$.

Ethyl 2-(2 fluoro-4-formyl-6-methoxyphenoxy)acetate

The compound was prepared according to general procedure E with 3-fluoro-4-hydroxy-5-methoxybenzaldehyde (1.8 mmol) in dry acetone (20 ml), anhydrous $K_2CO_3$ (2.4 mmol), and ethylbromoacetate (2.7 mmol) at reflux for 1 h. Ethanol was added and evaporated by azeotropic distillation with ethylbromoacetate. 395 mg of crude product were obtained and purified by silica gel chromatography (eluent dichloromethane). 361 mg of purified compound were obtained (79% yield). $^1$H NMR (500 MHz, $CD_3COCD_3$): δ 1.25 (t, J=, 3H), 3.98 (s, 3H), 4.21 (q, J=, 2H), 4.89 (s, 2H), 7.34 (dd, J=10.3 and 1.6 Hz, 1H), 7.40 (t, J=1.6 Hz, 1H), 9.88 (d, J=1.6 Hz, 1H) $^{13}$C NMR (126 MHz, $CD_3COCD_3$): δ 15.0, 57.6, 62.1, 70.3, 110.0, 111.8 (d, J=20.6 Hz), 133.1 (d, J=7.2 Hz), 141.8 (d, J=12.7 Hz), 154.5 (d, J=4.5 Hz), 156.0 (d, J=246 Hz), 169.7, 191.3. MS (ESI): m/z 256.9 $[M+H]^+$.

Ethyl 2-(2,6 dichloro-4-formyl-6-methoxyphenoxy)acetate

The compound was prepared according to general procedure E with 3,5-dichloro-4-hydroxybenzaldehyde (1.6 mmol) in dry acetone (15 ml), anhydrous $K_2CO_3$ (2.1 mmol), and ethylbromoacetate (2.4 mmol) at reflux for 1 h. Ethanol was added and evaporated by azeotropic distillation with ethylbromoacetate. 354 mg of crude product were obtained and purified by silica gel chromatography (eluent dichloromethane). 264 mg of purified compound were obtained (60% yield). $^1$H NMR (500 MHz, $CD_3COCD_3$): δ 1.32 (t, J=7.2 Hz, 3H), 4.30 (q, J=7.2 Hz, 2H), 4.74 (s, 2H), 7.82 (s, 2H), 9.67 (s, 1H) $^{13}$C NMR (126 MHz, $CD_3COCD_3$): δ 15.0, 62.3, 70.8, 131.2, 131.4, 135.4, 156.4, 168.4, 190.5

Ethyl 2-(2,6 dimethyl-4-formyl-6-methoxyphenoxy)acetate

The compound was prepared according to general procedure E with 3,5-dimethyl-4-hydroxybenzaldehyde (3.3 mmol) in dry acetone (20 ml), anhydrous $K_2CO_3$ (4.3 mmol), and ethylbromoacetate (5 mmol) at reflux for 1 h. Ethanol was added and evaporated by azeotropic distillation with ethylbromoacetate. 774 mg of crude product were obtained and purified by silica gel chromatography (eluent dichloromethane). 580 mg of purified compound were obtained (74% yield). $^1$H NMR (250 MHz, $CDCl_3$): δ 1.26 (t, J=7.2 Hz, 3H), 2.33 (s, 6H), 4.23 (q, J=7.2 Hz, 2H), 4.42 (s, 2H), 7.50 (s, 2H), 9.82 (s, 1H) $^{13}$C NMR (126 MHz, $CDCl_3$): δ 15.2, 17.4, 62.2, 70.1, 131.6, 132.8, 133.8, 161.7, 169.5, 192.1

Diisopropyl(4-formylphenoxy)methylphosphonate

The compound was prepared according to general procedure E with 4-hydroxybenzaldehyde (1.2 mmol) in dry DMF (20 ml), anhydrous $K_2CO_3$ (1.6 mmol), and diisopropyl bromomethyl phosphonate (1.9 mmol) heating at 110° C. overnight. Isopropanol was added and evaporated by azeotropic distillation with diisopropyl bromomethyl phosphonate. 418 mg of crude product were obtained and purified by silica gel chromatography (eluent: cyclohexane/ethyl acetate 5/5). 98 mg of purified compound were obtained (26% yield). $^1$H NMR (250 MHz, $CDCl_3$): δ 1.32 (d, J=6.0 Hz, 6H), 1.34 (d, J=6.0 Hz, 6H), 4.27 (d, J=10.2 Hz, 2H), 4.78 (q, J=6.0 Hz, 1H), 4.83 (q, 6.0 Hz, 1H), 7.05 (d, J=8.7 Hz, 2H), 7.82 (d, J=8.7 Hz, 2H), 9.87 (s, 1H) $^{13}$C NMR (126 MHz, $CDCl_3$): δ 25.3, 25.3, 25.4, 25.5 (4 $CH_3$ isopropyl), 63.7 (d, J=171 Hz), 73.2, 73.3 (2CH isopropyl), 116.3, 132.2, 133.3, 164.8, 192.0. $^{31}$P NMR (202 MHz, $CDCl_3$): δ 16.0. MS (ESI): m/z 300.9 $[M+H]^+$.

Ethyl 2-(2-ethoxy-4-formylphenoxy)acetate

The compound was prepared according to general procedure E with 3-ethoxy-4-hydroxybenzaldehyde (2.4 mmol) in dry acetone (15 ml), anhydrous $K_2CO_3$ (3.1 mmol), and ethylbromoacetate (3.6 mmol) at reflux for 1 h30. Ethanol was added and evaporated by azeotropic distillation with ethylbromoacetate. 565 mg of crude product were obtained and purified by silica gel chromatography (eluent dichloromethane). 385 mg of purified compound were obtained (63% yield). $^1$H NMR (250 MHz, $CDCl_3$): δ 1.31 (t, J=7.0 Hz, 3H), 1.49 (t, J=7.0 Hz, 3H), 4.18 (q, J=7.0 Hz, 2H), 4.31 (q, J=7.0 Hz, 2H), 4.79 (s, 2H), 6.91 (d, J=8.0 Hz, 1H), 7.42 (d, J=8.0 Hz, 1H), 7.45 (s, 1H) 9.86 (s, 1H) $^{13}$C NMR (63 MHz, $CDCl_3$): δ 14.0, 14.5, 61.2, 64.4, 65.9, 111.2, 113.0, 125.5, 131.0, 149.1, 152.7, 168.1, 191.5. MS (ESI): m/z 253.0 $[M+H]^+$.

Ethyl 2-(4-formyl-2-(trifluoromethoxyphenoxy))acetate

The compound was prepared according to general procedure E with 4-hydroxy-3-(trifluoromethoxy)benzaldehyde (1.5 mmol) in dry acetone (15 ml), anhydrous $K_2CO_3$ (1.9 mmol), and ethylbromoacetate (2.2 mmol) at reflux for 1 h. Ethanol was added and evaporated by azeotropic distillation with ethylbromoacetate. 311 mg of pure compound were obtained (73% yield). $^1$H NMR (250 MHz, $CDCl_3$): δ 1.22 (t, J=7.0 Hz, 3H), 4.19 (q, J=7.0 Hz, 2H), 4.76 (s, 2H), 6.99 (d, J=9.0 Hz, 1H), 7.72 (d, J=9.0 Hz, 1H), 7.74 (s, 1H) 9.82 (s, 1H) $^{13}$C NMR (63 MHz, $CDCl_3$): δ 13.8, 61.6, 65.6, 113.6, 120.5 (d, J=259 Hz), 123.3, 130.4, 130.5, 138.5, 155.1, 167.3, 189.4

Ethyl 2-(4-formyl-2-(trifluoromethyl)phenoxy)acetate

The compound was prepared according to general procedure E with 4-hydroxy-3-(trifluoromethyl)benzaldehyde (1.3 mmol) in dry acetone (20 ml), anhydrous $K_2CO_3$ (1.7 mmol), and ethylbromoacetate (2.2 mmol) at reflux for 1 h. Ethanol was added and evaporated by azeotropic distillation with ethylbromoacetate. The crude product was purified by silica gel chromatography (eluent dichloromethane). 215 mg of purified compound were obtained (59% yield). $^1$H NMR (250 MHz, $CDCl_3$): δ 1.30 (t, J=7.0 Hz, 3H), 4.28 (q, J=7.2 Hz, 2H), 4.85 (s, 2H), 7.02 (d, J=8.7 Hz, 1H), 8.04 (dd, J=8.9 and 2.0 Hz, 1H), 8.16 (d, J=2.0 Hz, 1H) 9.95 (s, 1H) $^{13}$C NMR (63

MHz, CDCl$_3$): δ 13.8, 61.6, 65.5, 112.9, 120.5 (d, J=32.0 Hz), 122.8 (d, J=273 Hz), 128.9, 129.6, 135.0, 160.1, 167.2, 189.6 MS (ESI): m/z 573.1 [2M+Na]$^+$.

Ethyl 2-(4-formyl-2-methoxyphenoxy)acetate

The compound was prepared according to general procedure E with vanillin (5.3 mmol) in dry acetone (20 ml), anhydrous K$_2$CO$_3$ (6.8 mmol), and ethylbromoacetate (6.3 mmol) at reflux for 1 h. Ethanol was added and evaporated by azeotropic distillation with ethylbromoacetate. 980 mg of pure compound were obtained (78% yield). $^1$H NMR (250 MHz, CDCl$_3$): δ 1.23 (m, 3H), 3.88 (s, 3H), 4.21 (m, 2H), 4.78 (s, 2H), 6.90 (m, 1H), 7.38 (m 2H), 9.80 (s, 1H) $^{13}$C NMR (63 MHz, CDCl$_3$): δ 13.9, 55.7, 61.2, 65.6, 109.8, 112.3, 125.7, 130.8, 149.7, 152.4, 167.9, 190.6 MS (ESI): m/z 253.0 [M+H]$^+$.

Ethyl 2-(4-formylphenoxy)propanoate

The compound was prepared according to general procedure E with 4-hydroxybenzaldehyde (3.3 mmol) in dry acetone (15 ml), anhydrous K$_2$CO$_3$ (4.3 mmol), and ethyl-2 bromopropionate (3.6 mmol) at reflux for 2 h45. Isopropanol was added and evaporated by azeotropic distillation with ethyl-2-bromopropionate. 609 mg of pure compound were obtained (83% yield). $^1$H NMR (250 MHz, CDCl$_3$): δ 1.10 (t, J=7.1 Hz, 3H), 1.52 (d, J=6.8 Hz, 3H), 4.10 (q, J=7.1 Hz, 2H), 4.76 (q, J=6.8 Hz, 1H) 6.85 (d, J=8.7 Hz 2H), 7.70 (d, J=8.9 Hz, 2H), 9.74 (s, 1H) $^{13}$C NMR (63 MHz, CDCl$_3$): δ 14.0, 18.2, 61.4, 72.4, 115.1, 130.4, 131.8, 162.4, 171.1, 190.5

Ethyl 2-(4-formyl-2-hydroxyphenoxy)acetate

The compound was prepared according to general procedure E with 3,4 dihydroxybenzaldehyde (3.7 mmol) in dry acetone (20 ml), anhydrous K$_2$CO$_3$ (2.3 mmol), and ethylbromoacetate (3.4 mmol) at 0°. The mixture was stirred at room temperature for 20 h. Ethanol was added and evaporated by azeotropic distillation with ethylbromoacetate The crude product was purified by silica gel chromatography (eluent dichloromethane). 112 mg of purified compound were obtained (15% yield). $^1$H NMR (250 MHz, CDCl$_3$): δ 1.31 (t, J=7.1 Hz, 3H), 4.28 (q, J=7.1 Hz, 2H), 4.78 (q, J=6.8 Hz, 1H) 6.95 (d, J=8.8 Hz, 1H), 7.46 (d, J=8.9 Hz, 1H), 7.55 (s, 1H), 9.86 (s, 1H) $^{13}$C NMR (63 MHz, CDCl$_3$): δ 15.2, 63.5, 67.1, 113.9, 117.1, 125.3, 132.8, 148.6, 152.4, 170.8, 193.3

2-ethoxy-2-oxoethyl 2-(2-ethoxy-2-oxoethoxy)-5-formylbenzoate

The compound was prepared according to general procedure E with syringaldehyde (2.1 mmol) in dry acetone (10 ml), anhydrous K$_2$CO$_3$ (2.7 mmol), and ethylbromoacetate (2.5 mmol) at reflux for 4 h. Ethanol was added and evaporated by azeotropic distillation with Ethylbromoacetate. The crude product was purified by silica gel chromatography (eluent dichloromethane). 221 mg of purified compound were obtained (31% yield). $^1$H NMR (250 MHz, CDCl$_3$): δ 1.30 (t, J=7.2 Hz, 3H), 4.24 (q, J=7.4 Hz, 2H), 4.81 (s, 2H), 4.84 (s, 2H), 6.98 (d, J=8.7 Hz, 1H), 8.0 (dd, J=8.9 and 1.9 Hz, 1H), 8.44 (d, J=1.9 Hz, 1H), 9.91 (s, 1H) $^{13}$C NMR (126 MHz, CDCl$_3$): δ 15.3, 62.7, 67.2, 115.0, 121.3, 131.2, 135.9, 135.9 (2C), 163.3, 165.0, 168.9, 191.2

Ethyl 2-(4-formyl-2-nitrophenylthio)acetate

To a solution of ethyl-2-mercaptoacetate (0.7 mmol) in dry DMF (2.5 ml), sodium hydride (0.85 mmol) was added 0° C.

After 15 minutes, 4-fluoro-3-nitrobenzaldehyde (0.7 mmol) was added and the mixture was heated at 60° C. overnight and monitored by TLC until completion. After cooling, the solvent was removed under reduced pressure. The residue was chromatogaphed on a silica gel column (cyclogexane/ethyl acetate 4/1 as eluent) to give 46 mg of ethyl 2-(4-formyl-2-nitrophenylthio)acetate as yellow compound (yield 24%). $^1$H NMR, (250 MHz, CDCl$_3$): δ 1.25 (t, J=7.5 Hz, 3H), 3.80 (s, 2H), 4.21 (q, J=7.75, 2H), 7.64 (d, J=9.75, 1H), 8.03 (d, J=9.75, 1H), 8.68 (s, 1H), 10.00 (s, 1H) $^{13}$C NMR (126 MHz, CDCl$_3$): δ 15.4, 36.5, 63.8, 128.5, 129.3, 133.9, 145.6, 147.1, 169.5, 190.1.

2-(4-formyl-2-nitrophenoxy)acetate

The compound was prepared according to general procedure E with 4-hydroxy-3-nitrobenzaldehyde (1.8 mmol) in dry DMF (15 ml), anhydrous K$_2$CO$_3$ (2.2 mmol), and ethylbromoacetate (2.2 mmol) at 80° C. overnight. Ethanol was added and evaporated by azeotropic distillation with ethylbromoacetate. The crude product was purified by silica gel chromatography (eluent cyclohexane/ethylacetate 9/1). 166 mg of purified compound were obtained (37% yield). $^1$H NMR (250 MHz, CDCl$_3$): δ 1.28 (t, J=7.25, 3H), 4.26 (q, 2H), 4.87 (s, 2H), 7.07 (d, J=9.75, 1H), 8.04 (d, J=9.75, 1H), 8.06 (s, 1H), 9.93 (s, 1H)

Ethyl 2-(4-formylphenythio)acetate

The compound was prepared according to general procedure E. To a solution of ethyl-2-mercaptoacetate (1.7 mmol) in dry DMF (5 ml), sodium hydride (2.0 mmol) was added at 0° C. After 10 minutes, 4-bromobenzaldehyde (1.4 mmol) was added and the mixture was heated for 3 hours. After cooling, the solvent was removed under reduced pressure. The residue was chromatogaphed on a silica gel column (cyclohexane/ethyl acetate 9/1 as eluent) to give 188 mg of ethyl 2-(4-formylphenythio)acetate (yield 59%). $^1$H NMR (250 MHz, CDCl$_3$): δ 1.23 (t, J=7.5 Hz, 3H), 3.73 (s, 2H), 4.18 (q, 2H), 7.42 (d, J=8.75 Hz, 2H), 7.76 (d, J=8.75 Hz, 2H), 9.93 (s, 1H).

Ethyl 2-(p-tolylamino)acetate

The compound was prepared according to general procedure E. To a solution of p-toluidine (4.7 mmol) in dry acetone (20 ml), ethylbromoacetate (4.7 mmol) was added. The mixture was refluxed for 3 hours. After cooling, the solvent was removed under reduced pressure. The residue was chromatogaphed on a silica gel column (dichloromethane/ethyl acetate 9/1 as eluent) to give 326 mg of ethyl 2-(p-tolylamino)acetate (yield 36%). $^1$H NMR (500 MHz, CDCl$_3$): δ 1.29 (t, J=7.4 Hz, 3H), 2.28 (s, 3H), 3.90 (s, 2H), 4.26 (q, J=7.4 Hz, 2H), 6.58 (d, J=8.2 Hz, 2H), 7.05 (d, J=8.2, 2H) $^{13}$C NMR (126 MHz, CDCl$_3$): δ 15.6, 21.8, 47.7, 62.5, 114.8, 131.2, 146.3, 172.8. MS (ESI): m/z 193.9 [M+H]$^+$ Ethyl 2-(4-formylphenylamino)acetate To a solution of ethyl 2-(p-tolylamino)acetate (1.69 mmol) in methanol/water (20 ml/20 ml) was added the 2,3 dichloro-5,6-dicyanobenzoquinone (2.87 mmol) and the mixture was stirred for 4 hours at room temperature. The residue was chromatographed on a silica gel column (dichloromethane/ ethyl acetate 8/2 as eluent) to give 88 mg of ethyl 2-(4-formylphenylamino)acetate. (yield 25%). MS (ESI): m/z 208.0 [M+H]$^+$

3,5-difluoro-4-hydroxybenzaldehyde

A stirring solution of 2,6-difluorophenol (2 g, 15.4 mmol) and hexamethylenetetramine (2.16 g, 15.4 mmol) in TFA (16 mL) was heated at reflux under argon overnight. On cooling to room temperature the solvent was evaporated in vacuum and the crude residue was taken up in DCM (35 mL). The mixture was washed with an aqueous solution of $NaHCO_3$ (sat.) and the separated aqueous layer acidified to pH 1 with concentrated HCl. The aqueous layer was extracted with DCM (2×25 mL), the combined organic fractions dried ($MgSO_4$) and evaporated in vacuum to afford desired product as a cream solid (1.76 g, 73%). Rf=0.39 ($SiO_2$; cyclohexane/EtOAc (6/4); UV) $^1$H NMR (300 MHz; $CDCl_3$) δ: 6.38 (br, 1H); 7.50 (d, 2H, J=6.6 Hz); 9.82 (s, 1H). $^{13}$C NMR (75 MHz; $CDCl_3$) δ: 113.2 (dd, $J_{CF}$=13.8 Hz and 7.8 Hz); 128.2 (t, $J_{CF}$=6.0 Hz); 139.0 (t, $J_{CF}$=16.1 Hz); 151.9 (dd, $J_{CF}$=246.9 Hz and 5.3 Hz); 189.1. $^{19}$F NMR (282 MHz; $CDCl_3$) δ: −52.2

Synthesis of ethyl 2-(2,6-difluoro-4-formylphenoxy)acetate 656 mg (4.74 mmol) of $K_2CO_3$ and 0.44 mL (3.95 mmol) of ethyl 2-bromoacetate were added to a solution of 3,5-difluoro-4-hydroxybenzaldehyde (0.5 g, 3.16 mmol) in 40 mL of acetone. The reaction mixture was refluxed under argon during 1 hour. After cooling, acetone was evaporated under vacuum. The mixture was diluted in 40 mL of DCM and washed with brine (3×). The combined organic phase was dried under $MgSO_4$. Evaporation of the solvent and chromatography of the oily residue [$SiO_2$, cyclochexane/DCM (8/2)] afforded a yellowish oil (580 mg, 75%). Rf=0.23 ($SiO_2$; cyclohexane/DCM:1/1; UV). $^1$H NMR (250 MHz; $CDCl_3$) δ (ppm): 1.31 (t, 3H, J=7.5 Hz); 4.28 (q, 2H, J=7.5 Hz); 4.92 (s, 2H); 7.48 (d, 2H, J=8.75 Hz); 9.86 (s, 1H). $^{13}$C NMR (125 MHz; $CDCl_3$) δ (ppm): 15.5; 63.1; 70.6; 114.9 (dd, $J_{CF}$=17.6 Hz and 6.0 Hz); 132.1 (t, $J_{CF}$=7.0 Hz); 141.3 (t, $J_{CF}$=13.6 Hz); 156.3 (dd, $J_{CF}$=251.1 Hz and 5.6 Hz); 169.4; 190.1. $^{19}$F NMR (282 MHz; $CDCl_3$) δ (ppm): −50.9.

Ethyl 2-(2-chloro-4-(hydroxymethyl)-6-methoxyphenoxy)acetate

The compound was prepared according to general procedure F with Ethyl 2-(2-chloro-4-formyl-6-methoxyphenoxy)acetate (1.5 mmol) in THF (20 ml) and water (20 ml) and $NaBH_4$ (1.5 mmol). 355 mg of compound were obtained. This compound was used without further purification. $^1$H NMR (250 MHz, $CDCl_3$): δ 1.31 (t, J=7.1 Hz, 3H), 3.86 (s, 3H), 4.25 (q, J=7.1 Hz, 2H), 4.55 (s, 2H), 4.60 (s, 2H) 6.95 (s, 1H), 6.98 (s, 1H). MS (ESI): m/z 274.9 and 276.9 [M+H]$^+$, 570.7 and 572.7 [2M+Na]$^+$

Ethyl 2-(2 fluoro-4-(hydroxymethyl)-6-methoxyphenoxy)acetate

The compound was prepared according to general procedure F with Ethyl 2-(2-fluoro-4-formyl-6-methoxyphenoxy) acetate (1.4 mmol) in THF (20 ml) and water (20 ml) and $NaBH_4$ (1.4 mmol). 220 mg of compound were obtained. This compound was used without further purification. $^1$H NMR (250 MHz, $CDCl_3$): δ 1.33 (t, J=7.1 Hz, 3H), 3.90 (s, 3H), 4.28 (q, J=7.1 Hz, 2H), 4.65 (s, 2H), 4.71 (s, 2H) 6.95 (s, 1H), 6.76 (m, 2H). MS (ESI): m/z 538.8 [2M+Na]$^+$

Ethyl 2-(4-hydroxymethyl-2-(trifluoromethoxyphenoxy))acetate

The compound was prepared according to general procedure F with ethyl 2-(4-formyl-2-(trifluoromethoxyphenoxy)) acetate (2.5 mmol) in THF (40 ml) and water (40 ml) and $NaBH_4$ (2.7 mmol). 526 mg of crude product were obtained and purified by silica gel chromatography (eluent dichloromethane). 140 mg of purified compound were obtained (19% yield). $^1$H NMR (250 MHz, $CDCl_3$): δ 1.26 (t, J=7.1 Hz, 3H), 2.97 (s, 1H, OH), 4.22 (q, J=7.2 Hz, 2H), 4.54 (s, 2H), 4.67 (s, 2H) 6.85 (d, J=8.6 Hz, 1H), 7.15 (d, J=8.3 Hz, 1H), 7.24 (s, 1H).) $^{13}$C NMR (63 MHz, $CDCl_3$): δ 13.9, 61.5, 63.6, 66.2, 114.4, 120.6 (d, J=257 Hz), 121.7, 126.1, 135.4, 138.2, 149.4, 168.6. MS (ESI): m/z 610.7 [2M+Na]$^+$

Ethyl 2-(4-hydroxymethyl-2-(trifluoromethylphenoxy))acetate

The compound was prepared according to general procedure F with ethyl 2-(4-formyl-2-(trifluoromethylphenoxy)) acetate (2.7 mmol) in THF (40 ml) and water (40 ml) and $NaBH_4$ (2.9 mmol). 611 mg of crude product were obtained and purified by silica gel chromatography (eluent dichloromethane/ethyl acetate 9:1). 408 mg of purified compound were obtained (55% yield). $^1$H NMR (250 MHz, $CDCl_3$): δ 1.27 (t, J=7.0 Hz, 3H), 3.29 (s, 1H, OH), 4.24 (q, J=7.1 Hz, 2H), 4.53 (s, 2H), 4.67 (s, 2H) 6.81 (d, J=8.4 Hz, 1H), 7.37 (d, J=8.2 Hz, 1H), 7.53 (s, 1H).) $^{13}$C NMR (63 MHz, $CDCl_3$): δ 13.9, 61.6, 63.7, 65.8, 113.0, 119.6 (q, J=30.4 Hz) 123.4 (d, J=273 Hz), 126.1 (q, J=5.1 Hz), 131.7, 134.1, 155.0, 168.4. MS (ESI): m/z 300.9 [M+Na]$^+$

Ethyl 2-(4-hydroxymethyl-2-methoxyphenoxy))acetate

The compound was prepared according to general procedure F with ethyl 2-(4-formyl-2-methoxyphenoxy)acetate (5.9 mmol) in THF (40 ml) and water (40 ml) and $NaBH_4$ (6.5 mmol). 437 mg of crude product were obtained and purified by silica gel chromatography (eluent dichloromethane). 249 mg of purified compound were obtained (18% yield). $^1$H NMR (250 MHz, $CDCl_3$): δ 1.19 (t, J=7.0 Hz, 3H), 3.15 (s, 1H, OH), 3.74 (s, 3H) 4.15 (q, J=7.1 Hz, 2H), 4.46 (s, 2H), 4.55 (s, 2H) 6.70 (s, 1H), 6.71 (s, 1H), 6.83 (s, 1H).) $^{13}$C NMR (63 MHz, $CDCl_3$): δ 14.1, 55.7, 61.2, 64.5, 66.5, 111.0, 114.3, 118.9, 135.7, 146.4, 149.6, 169.1. MS (ESI): m/z 502.7 [2M+Na]$^+$

Ethyl 2-(4-(bromomethyl)-2-chloro-6-methoxyphenoxy)acetate

The compound was prepared according to general procedure G with ethyl 2-(2-chloro-4-(hydroxymethyl)-6-methoxyphenoxy)acetate (1.3 mmol) in dichloromethane (12 ml) and $PBr_3$ (1.3 mmol). 338 mg of compound were obtained (78% yield). This compound was used without further purification. $^1$H NMR (250 MHz, $CD_3OD$): δ 1.29 (m, 3H), 3.83 (s, 3H), 4.15 (m, 2H), 4.55 (s, 2H), 4.94 (s, 2H) 6.80 (d, J=2.0 Hz, 1H), 6.85 (d, J=2.0 Hz, 1H). MS (ESI): m/z 336.9 [M−H]$^-$, 360.8 [M+Na]$^+$

Ethyl 2-(4-(bromomethyl)-2-fluoro-6-methoxyphenoxy)acetate

The compound was prepared according to general procedure G with ethyl 2-(2-fluoro-4-(hydroxymethyl)-6-methoxyphenoxy)acetate (0.4 mmol) in dichloromethane (5 ml) and $PBr_3$ (0.4 mmol). 67 mg of compound were obtained (54% yield). This compound was used without further purification. $^1$H NMR (250 MHz, $CDCl_3$): δ 1.29 (t, J=7.0 Hz, 3H), 3.89 (s, 3H), 4.25 (q, J=7.0 Hz, 2H), 4.41 (s, 2H), 4.71 (s, 2H) 6.74 (m, 1H), 6.81 (m, 1H). MS (ESI): m/z 319.9 [M+H]$^+$ Ethyl 2-(4-(bromomethyl)-2-(trifluoromethoxy)phenoxy)acetate The compound was prepared according to general procedure G with ethyl 2-(4-hydroxymethyl-2-(trifluoromethoxyphenoxy))acetate (0.5 mmol) in dichloromethane (5 ml) and PBr$_3$ (0.5 mmol). 139 mg of compound were obtained (82% yield). This compound was used without further purification. $^1$H NMR (250 MHz, CDCl$_3$): δ 1.28 (t, J=7.2 Hz, 3H), 4.26 (q, J=7.0 Hz, 2H), 4.44 (s, 2H), 4.69 (s, 2H), 7.25 (d, J=8.6 Hz, 1H), 7.27 (d, J=8.7 Hz, 1H), 7.32 (s, 1H). $^{13}$C NMR (126 MHz, CDCl$_3$): δ 13.6, 31.7, 61.2, 65.8, 114.1, 122.0 (d, J=258 Hz), 123.6, 128.1, 131.5, 137.9, 150.0, 167.7. MS (ESI): m/z 378.9 (100%), 379.8 (13%), 380.9 (100%), 381.9 (13%) [M+Na]$^+$ Ethyl 2-(4-(bromomethyl)-2-(trifluoromethylphenoxy))acetate The compound was prepared according to general procedure G with ethyl 2-(4-hydroxymethyl-2-(trifluoromethylphenoxy))acetate (1.5 mmol) in dichloromethane (10 ml) and PBr$_3$ (1.5 mmol). 421 mg of compound were obtained (82% yield). This compound was used without further purification. $^1$H NMR (500 MHz, CDCl$_3$): δ 1.26 (t, J=7.1 Hz, 3H), 4.10 (q, J=7.1 Hz, 2H), 4.46 (s, 2H), 4.70 (s, 2H), 6.86 (d, J=8.6 Hz, 1H), 7.49 (dd, J=8.7 and 2.1 Hz, 1H), 7.62 (d, J=2.1 Hz, 1H). $^{13}$C NMR (126 MHz, CDCl$_3$): δ 15.4, 33.5, 63.0, 67.2, 114.6, 121.0 (q, J=32.0 Hz), 124.0 (d, J=272.0 Hz), 128.6, 132.3, 135.3, 157.1, 169.3.

Ethyl 2-(4-(bromomethyl)-2-methoxyphenoxy)acetate

The compound was prepared according to general procedure G with ethyl 2-(4-hydroxymethyl-2-methoxyphenoxy))acetate (1.0 mmol) in dichloromethane (5 ml) and PBr$_3$ (1.0 mmol). 261 mg of compound were obtained (83% yield). This compound was used without further purification. $^1$H NMR (500 MHz, CDCl$_3$): δ 1.23 (t, J=7.2 Hz, 3H), 3.81 (s, 3H) 4.22 (q, J=7.2 Hz, 2H), 4.42 (s, 2H), 4.62 (s, 2H), 6.71 (d, J=8.3 Hz, 1H), 6.84 (dd, J=8.3 and 1.9 Hz, 1H), 6.89 (d, J=1.9 Hz, 1H). $^{13}$C NMR (126 MHz, CDCl$_3$): δ 14.2, 34.0, 55.9, 61.3, 66.4, 112.9, 114.0, 121.4 131.9, 147.4, 149.6, 168.7 MS (ESI): m/z 324.9 (100%), 325.9 (13%), 326.8 (100%), 327.9 (13%) [M+Na]$^+$ 3-(benzyloxycarbonylamino)-4-methoxy-4-oxobutyl ((3-ethoxy-4-(2-ethoxy-2-oxoethoxy)phenyl)(hydroxy)methyl)phosphinic acid The compound was prepared according to general procedure B with H-phosphinic acid 1 (1.5 mmol), ethyl 2-(2-ethoxy-4-formylphenoxy)acetate (1.5 mmol) and BSA (6.1 mmol). 1.5 g of crude product were obtained and used without further purification. $^{31}$P NMR (101 MHz, CD$_3$OH): δ 47.9. MS (ESI): m/z 566.1 [M−H]$^-$ 3-(benzyloxycarbonylamino)-4-methoxy-4-oxobutyl ((4-(2-ethoxy-2-oxoethoxy)-3-(trifluoromethoxy) phenyl)(hydroxy)methyl)phosphinic acid The compound was prepared according to general procedure B with H-phosphinic acid 1 (1.0 mmol), ethyl 2-(4-formyl-2-(trifluoromethoxyphenoxy))acetate (1.0 mmol) and BSA (4.2 mmol). 684 mg of crude product were obtained and used without further purification. $^{31}$P NMR (101 MHz, CD$_3$OH): δ 47.9. MS (ESI): m/z 607.9 [M+H]$^+$ and 1214.9 [2M+H]$^+$ 3-(benzyloxycarbonylamino)-4-methoxy-4-oxobutyl ((4-(2-ethoxy-2-oxoethoxy)-3-(trifluoromethyl)phenyl)(hydroxy)methyl)phosphinic acid The compound was prepared according to general procedure B with H-phosphinic acid 1 (0.8 mmol), ethyl 2-(4-formyl-2-(trifluoromethylphenoxy)) acetate (0.8 mmol) and BSA (3.12 mmol). 219 mg of crude product were obtained and used without further purification. $^{31}$P NMR (101 MHz, CDCl$_3$): δ 50.8

3-(benzyloxycarbonylamino)-4-methoxy-4-oxobutyl ((4-(2-ethoxy-2-oxoethoxy)-3-hydroxyphenyl)(hydroxy)methyl)phosphinic acid The compound was prepared according to general procedure B with H-phosphinic acid 1 (0.6 mmol), ethyl 2-(4-formyl-2-hydroxyphenoxy)acetate (0.6 mmol) and BSA (2.4 mmol). 308 mg of crude product were obtained and used without further purification. $^{31}$P NMR (101 MHz, CDCl$_3$): δ 47.7

3-(benzyloxycarbonylamino)-4-methoxy-4-oxobutyl ((4-(2-ethoxy-2-oxoethoxy)-3-((2-ethoxy-2-oxoethoxy)carbonyl)phenyl)(hydroxy)methyl)phosphinic acid The compound was prepared according to general procedure B with H-phosphinic acid 1 (0.7 mmol), ethyl 3-(2-(2-etoxy-2-oxo ethoxy)-5-formylphenyl)-3-oxopropanoate (0.7 mmol) and BSA (2.8 mmol). 467 mg of crude product were obtained and used without further purification. $^{31}$P NMR (101 MHz, CDCl$_3$): δ 50.3. MS (ESI): m/z 652.1 [M−H]$^-$ 3-(benzyloxycarbonylamino)-4-methoxy-4-oxobutyl (4-(2-ethoxy-2-oxoethoxy)-3-nitrobenzyl)phosphinic acid The compound was prepared according to general procedure B with H-phosphinic acid 1 (0.66 mmol), 2-(4-formyl-2-nitrophenoxy)acetate (0.66 mmol) and BSA (2.64 mmol). 492 mg of crude product were obtained and used without further purification. $^{31}$P NMR (101 MHz, CDCl$_3$): δ=39.7

3-(benzyloxycarbonylamino)-4-methoxy-4-oxobutyl (4-(2-ethoxy-2-oxoethylthio)-3-nitrobenzyl)phosphinic acid The compound was prepared according to general procedure B with H-phosphinic acid 1 (0.17 mmol), ethyl 2-(4-formyl-2-nitrophenylthio)acetate (0.17 mmol) and BSA (0.68 mmol). 140 mg of crude product were obtained and used without further purification.

3-(benzyloxycarbonylamino)-4-methoxy-4-oxobutyl (4-(2-ethoxy-2-oxoethylthio)benzyl)phosphinic acid The compound was prepared according to general procedure B with H-phosphinic acid 1 (0.84 mmol), ethyl 2-(4-formylphenythio)acetate (0.84 mmol) and BSA (3.36 mmol).

294 mg of crude product were obtained and used without further purification. $^{31}$P NMR (101 MHz, CDCl$_3$): δ=41.9

3-(benzyloxycarbonylamino)-4-methoxy-4-oxobutyl (4-(2-ethoxy-2-oxoethylamino)benzyl)phosphinic acid The compound was prepared according to general procedure B with H-phosphinic acid 1 (0.43 mmol), ethyl 2-(4-formylphenylamino)acetate (0.43 mmol) and BSA (1.7 mmol). 367 mg of crude product were obtained and used without further purification. $^{31}$P NMR (101 MHz, CDCl$_3$): δ=48.0

3-(((benzyloxy)carbonyl)amino)-4-methoxy-4-oxobutyl)((4-(2-ethoxy-2-oxoethoxy)-3,5-difluorophenyl)(hydroxy)methyl)phosphinic acid The compound was prepared according to general procedure B with H-phosphinic acid 1 (0.99 mmol), ethyl 2-(4-formylphenylamino)acetate (0.99 mmol) and BSA (3.96 mmol). 552 mg of crude product were obtained and used without further purification. $^{31}$P NMR (101 MHz, CDCl$_3$): δ=50.0

3-(benzyloxycarbonylamino)-4-methoxy-4-oxobutyl ((4-(1-ethoxy-1-oxopropan-2-yloxy)phenyl)(hydroxy)methyl)phosphinic acid The compound was prepared according to general procedure B with H-phosphinic acid 1 (2.7 mmol), ethyl 2-(4-formylphenoxy)propanoate (2.7 mmol) and BSA (11.0 mmol). 750 mg of crude product were obtained and used without further purification. $^{31}$P NMR (101 MHz, CDCl$_3$): δ 47.7. MS (ESI): m/z 536.1 [M−H]$^−$

[((3S)-3-(N-Benzyloxycarbonyl)amino-3-methoxycarbonyl)propyl][(4-(carboxymethoxy)phenyl)methyl]phosphinic Acid The compound was prepared according to general procedure B with H-phosphinic acid 1 (315 mg, 1.0 mmol) and 4-bromomethyl-phenoxyacetic acid (539 mg, 2.2 mmol). 967 mg of crude product were obtained. $^{31}$P NMR (101 MHz, CD$_3$OD): δ 50.7.

3-(benzyloxycarbonylamino)-4-methoxy-4-oxobutyl (4-(2-ethoxy-2-oxoethoxy)-3-methoxybenzyl)phosphinic acid The compound was prepared according to general procedure B with H-phosphinic acid 1 (0.9 mmol), ethyl 2-(4-(bromomethyl)-2-methoxyphenoxy)acetate (0.9 mmol) and BSA (3.5 mmol). 555 mg of crude product were obtained and used without further purification. $^{31}$P NMR (101 MHz, MeOD): δ 53.0. MS (ESI): m/z 536.0 [M−H]$^−$ and 1072.9 [2M−H]$^−$

3-(benzyloxycarbonylamino)-4-methoxy-4-oxobutyl (4-(2-ethoxy-2-oxoethoxy)-3-(trifluoromethoxy)benzyl)phosphinic acid The compound was prepared according to general procedure B with H-phosphinic acid 1 (0.4 mmol), ethyl 2-(4-(bromomethyl)-2-(trifluoromethoxy)phenoxy)acetate (0.4 mmol) and BSA (1.6 mmol). 293 mg of crude product were obtained and used without further purification. $^{31}$P NMR (101 MHz, MeOD): δ 51.2. MS (ESI): m/z 590.0 [M−H]$^−$ and 1180.9 [2M−H]$^−$

3-(benzyloxycarbonylamino)-4-methoxy-4-oxobutyl (4-(2-ethoxy-2-oxoethoxy)-3-(trifluoromethyl)benzyl)phosphinic acid The compound was prepared according to general procedure B with H-phosphinic acid 1 (0.8 mmol), ethyl 2-(4-(bromomethyl)-2-(trifluoromethyl)phenoxy)acetate (0.8 mmol) and BSA (3.2 mmol). 555 mg of crude product were obtained and used without further purification. $^{31}$P NMR (101 MHz, MeOD): δ 48.6. MS (ESI): m/z 574.0 [M−H]$^−$ and 1148.8 [2M−H]$^−$

3-(benzyloxycarbonylamino)-4-methoxy-4-oxobutyl (4-(2-ethoxy-2-oxoethoxy)-3-fluoro-5-methoxybenzyl)phosphinic acid The compound was prepared according to general procedure B with H-phosphinic acid 1 (0.6 mmol), ethyl 2-(4-(bromomethyl)-2-fluoro-6-methoxyphenoxy)acetate (0.6 mmol) and BSA (2.5 mmol). 510 mg of crude product were obtained and used without further purification. $^{31}$P NMR (101 MHz, MeOD): δ 48.5

3-(benzyloxycarbonylamino)-4-methoxy-4-oxobutyl (3-chloro-4-(2-ethoxy-2-oxoethoxy)-5-methoxybenzyl)phosphinic acid The compound was prepared according to general procedure B with H-phosphinic acid 1 (1 mmol), ethyl 2-(4-(bromomethyl)-2-chloro-6-methoxyphenoxy)acetate (1 mmol) and BSA (4 mmol). 307 mg of crude product were obtained and used without further purification. $^{31}$P NMR (101 MHz, MeOD): δ 41.9. MS (ESI): m/z 569.9 [M−H]$^−$

Derivative 19

2-amino-4-(((4-(carboxymethoxy)-3-ethoxyphenyl)(hydroxy)methyl)(hydroxy)phosphoryl)butanoic acid The compound was prepared according to general procedure C applied to the protected derivative. The purification was performed using a Dowex AG 50W-X4 cation exchange resin column (H$^+$, 50-100 mesh, water elution). Another purification was made on an anion exchange chromatography (Dowex AG 1-X4, AcO$^−$, 200-400 mesh). The resin was first eluted with freshly boiled and cooled water, then with formic acid 2.5M. 37 mg of pure derivative 19 were obtained (6% yield in 2 steps)). $^1$H NMR (250 MHz, D$_2$O): δ 1.34 (t, J=7 Hz, 3H), 1.77 (m, 2H), 2.08 (m, 2H), 4.03 (m, 1H), 4.08 (q, J=7 Hz, 2H), 4.70 (s, 2H), 4.88 (d, J=8 Hz), 6.92 (m, 2H), 7.07 (s, 1H). $^{31}$P NMR (101 MHz, D$_2$O): δ 44.4. $^{13}$C NMR (63 MHz, D$_2$O): δ 13.8, 21.7 (d, J=123 Hz), 22.6, 52.9, 65.1, 65.6, 71.8 (d, J=110 Hz), 112.5, 113.6, 119.8, 130.8, 146.5, 147.5, 171.3, 173.1. MS (ESI): m/z 383.9 [M+H]$^+$, 391.9[M−H]$^−$. HPLC MS t$_R$=8.27 min.

Derivative 20

2-amino-4-(((4-(carboxymethoxy)-3-(trifluoromethoxy)phenyl)(hydroxy)methyl)(hydroxy)phosphoryl)butanoic acid The compound was prepared according to general procedure C applied to the protected derivative. The purification was performed using a Dowex AG 50W-X4 cation exchange resin column (H+, 50-100 mesh, water elution. 127 mg of pure derivative 20 were obtained (28% yield in 2 steps). $^1$H NMR (250 MHz, D$_2$O): δ 1.67 (m, 2H), 2.06 (m, 2H), 3.90 (m, 1H), 4.80 (m, 3H), 7.06 (d, J=8 Hz, 1H), 7.33 (d, J=8 Hz, 1H), 7.40 (s, 1H). $^{31}$P NMR (101 MHz, D$_2$O): δ 38.4. $^{13}$C NMR (63 MHz, D$_2$O): δ 22.2 (d, J=85 Hz), 23.2, 54.1, 65.8, 71.8 (d, J=109 Hz), 114.5, 120.4 (d, J=258 Hz), 121.5, 126.6, 132.1, 137.5, 149.0, 172.1 173.8. MS (ESI): m/z 431.9 [M+H]+, 430.0[M−H]−. HPLC MS t$_R$=12.52 min.

Derivative 21

2-amino-4-(((4-(carboxymethoxy)-3-(trifluoromethyl)phenyl)(hydroxy)methyl)(hydroxy)phosphoryl) butanoic acid The compound was prepared according to general procedure C applied to the protected derivative. The purification was performed using a Dowex AG 50W-X4 cation exchange resin column (H+, 50-100 mesh, water elution). Another purification was made on an anion exchange chromatography (Dowex AG 1-X4, AcO−, 200-400 mesh). The resin was first eluted with freshly boiled and cooled water, then with formic acid. 16 mg of pure derivative 21 were obtained (4% yield in 2 steps). $^1$H NMR (500 MHz, D$_2$O): δ 1.73 (m, 2H), 2.08 (m, 2H), 3.99 (q, J=6 Hz, 1H), 4.82 (s, 2H), 4.84 (d, J=8 Hz, 1H), 7.07 (d, J=9 Hz, 1H), 7.57 (d, J=8 Hz, 1H), 7.68 (s, 1H). $^{31}$P NMR (101 MHz, D$_2$O): δ 39.1 $^{13}$C NMR (126 MHz, D$_2$O): δ 23.1 (d, J=87 Hz), 24.6, 55.3, 67.3, 73.3 (d, J=107 Hz), 115.1, 119.5 (d, J=31 Hz), 125.0 (d, J=273 Hz), 127.3, 132.4, 133.7, 156.3, 173.5, 174.5. MS (ESI): m/z 415.9 [M+H]+. HPLC MS t$_R$=12.74 min.

Derivative 22

2-amino-4-(((4-(carboxymethoxy)-3-hydroxyphenyl) (hydroxy)methyl)(hydroxy)phosphoryl)butanoic acid (derivative 22)

The compound was prepared according to general procedure C applied to the protected derivative. The purification was performed using a Dowex AG 50W-X4 cation exchange resin column (H+, 50-100 mesh, water elution). Another purification was made on an anion exchange chromatography (Dowex AG 1-X4, AcO−, 200-400 mesh). The resin was first eluted with freshly boiled and cooled water, then with formic acid 2.3M. 17.9 mg of pure derivative 22 were obtained (9% yield in 2 steps). $^1$H NMR (500 MHz, D$_2$O): δ 1.72 (m, 2H), 2.04 (m, 2H), 3.95 (t, J=6.8 Hz, 1H), 4.72 (s, 2H), 4.73 (d, J=9 Hz, 1H), 6.89 (m, 2H), 6.96 (s, 1H). $^{31}$P NMR (101 MHz, D$_2$O): δ 40.3 $^{13}$C NMR (126 MHz, D$_2$O): δ 23.5 (d, J=89 Hz), 24.6 (d, J=2 Hz), 55.2 (d, J=15 Hz), 67.4, 73.8 (d, J=110 Hz) 115.1, 116.2, 120.8, 127.5, 133.4, 146.4, 146.7, 173.6, 175.2. MS (ESI): m/z 363.9 [M+H]+. HPLC MS t$_R$=6.49 min.

Derivative 23

5-(((3-amino-3-carboxypropyl)(hydroxy)phosphoryl) (hydroxy)methyl)-2-(carboxymethoxy)benzoic acid The compound was prepared according to general procedure C applied to the protected derivative. The purification was performed using a Dowex AG 50W-X4 cation exchange resin column (H+, 50-100 mesh, water elution). Another purification was made on an anion exchange chromatography (Dowex AG 1-X4, AcO−, 200-400 mesh). The resin was first eluted with freshly boiled and cooled water, then with formic acid 4M. 40 mg of pure derivative 23 were obtained (16% yield in 2 steps). $^1$H NMR (500 MHz, D$_2$O): δ 1.71 (m, 2H), 2.06 (m, 2H), 3.96 (q, J=5.7 Hz, 1H), 4.80 (s, 2H), 4.82 (d, J=8.8 Hz, 1H), 7.04 (d, J=8.8 Hz, 1H), 7.56 (d, J=8.8 Hz, 1H), 7.82 (s, 1H). $^{31}$P NMR (101 MHz, D$_2$O): δ 39.4 $^{13}$C NMR (126 MHz, D$_2$O): δ 23.6 (d, J=90 Hz), 24.6, 55.1, 67.6, 73.3 (d, J=108 Hz), 115.5, 120.8, 131.6, 132.9, 134.6, 157.7, 171.1, 173.5, 174.7 MS (ESI): m/z 392.0 [M+H]+. HPLC MS t$_R$=6.93 min.

Derivative 24

2-amino-4-(((4-(carboxymethoxy)-3-nitrophenyl) (hydroxy)methyl)(hydroxy)phosphoryl)butanoic acid The compound was prepared according to general procedure C applied to the protected derivative. The purification was performed using a Dowex AG 50W-X4 cation exchange resin column (H+, 50-100 mesh, water elution). 75 mg of pure derivative 24 were obtained (29% yield in 2 steps). $^1$H NMR (250 MHz, D$_2$O): δ 1.74 (m, 2H), 2.09 (m, 2H), 4.00 (m, 1H), 4.86 (s, 2H), 4.85 (d, J=8.5 Hz, 1H), 7.16 (d, J=9.25, 1H), 7.63 (d, J=9.25, 1H), 7.97 (s, 1H). $^{13}$C NMR (63 MHz, D$_2$O): δ 22.2 (d, J=87 Hz), 23.3, 53.5, 66.3, 71.5 (d, J=107 Hz), 115.5, 124.4, 132.0, 133.7, 138.9, 150.5, 171.8, 172.6. $^{31}$P NMR (101 MHz, D$_2$O) δ 39.7. MS (ESI): m/z 393.0 [M+H]+. HPLC MS: t$_R$=8.02 min Derivative 25

2-amino-4-(((4-(carboxymethylthio)-3-nitrophenyl) (hydroxy)methyl)(hydroxy)phosphoryl)butanoic acid The compound was prepared according to general procedure C applied to the protected derivative. The purification was performed using a Dowex AG 50W-X4 cation exchange resin column (H+, 50-100 mesh, water elution). 17 mg of pure derivative 25 were obtained (24% yield in 2 steps). $^1$H NMR (250 MHz, D$_2$O): δ 1.92 (m, 2H), 2.11 (m, 2H), 3.97 (m, 3H), 4.87 (d, J=9.75, 1H), 7.45 (d, J=7.5, 1H), 7.65 (d, J=7.75, 1H), 8.24 (s, 1H) $^{13}$C NMR (500 MHz, D$_2$O): δ 23.8 (d, J=87 Hz), 250, 36.3, 55.4, 73.2 (d, J=107 Hz), 125.7, 128.7, 134.3, 135.8, 138.7, 147.5, 173.7, 174.9. $^{31}$P NMR (101 MHz, D$_2$O) δ 38.5. MS (ESI): m/z 408.9.0 [M+H]+.

Derivative 26

2-amino-4-(((4-(carboxymethylthio)phenyl)(hydroxy)methyl)(hydroxy)phosphoryl)butanoic acid The compound was prepared according to general procedure C applied to the protected derivative. The purification was performed using a Dowex AG 50W-X4 cation exchange resin column (H+, 50-100 mesh, water elution). 88 mg of pure derivative 26 were obtained (28% yield in 2 steps). $^1$H NMR (250 MHz, D$_2$O): δ 1.70 (m, 2H), 2.06 (m, 2H), 3.78 (s, 2H,) 3.93 (m, 1H), 4.81 (d, J=9.5 Hz, 1H), 7.40 (m, 4H) $^{13}$C NMR (250 MHz, D$_2$O): δ 21.5 (d, J=87 Hz), 21.6, 34.6, 52.0, 71.2 (d, J=111 Hz), 125.1, 126.2, 128.2, 132.6, 135.6, 139.9, 170.8, 172.8. $^{31}$P NMR (101 MHz, D$_2$O): δ=41.92. MS (ESI): m/z 363.9 [M+H]$^+$. HPLC-MS: t$_R$=9.38 min

Derivative 28

2-amino-4-(((4-(carboxymethoxy)-3,5-difluorophenyl)(hydroxy)methyl)(hydroxy)phosphoryl)butanoic acid A solution of ((S)-3-(((benzyloxy)carbonyl)amino)-4-methoxy-4-oxobutyl)((4-(2-ethoxy-2-oxoethoxy)-3,5-difluorophenyl)(hydroxy)methyl)phosphinic acid (552 mg, 0.99 mmol) in 6 N HCl (6M) was refluxed during 3 h. Then, the mixture was cooled to room temperature and the solvent was evaporated under vacuum. The residue was diluted in EtOAc (50 mL) and extracted with 1 N HCl (2×80 mL). The combined aqueous layers were washed twice with EtOAc and the solvent was evaporated to afford 238 mg (0.62 mmol) of crude product which was purified by cation (and anion) exchange resin chromatography. Cation exchange resin chromatography: 238 mg of crude compound were deposited on a Dowex AG 50W-X4, H$^+$, 50-100 mesh. The compound was eluted with water and 85 mg of desired product were collected. Anion exchange resin chromatography: 85 mg of compound were deposited on a Dowex AG 50W-X4, AcO$^-$, 200-400 mesh. The compound was eluted with boiled water and formic acid. 27 mg (yield 7% on 2 steps) of pure product derivative 28 were collected (2 M HCOOH). $^1$H NMR (250 MHz; D$_2$O) δ (ppm): 1.87 (m, 2H); 2.17 (m, 2H); 4.13 (m, 1H); 4.87 (s, 2H); 4.94 (d, J$_{HP}$=9.4 Hz, 1H); 7.13 (d, J=9.1 Hz, 2H). $^{13}$C NMR (63 MHz; D$_2$O) δ (ppm): 21.7 (d, JCP=91.0 Hz); 22.8; 53.1 (d, JCP=14.8 Hz); 69.8; 71.3 (d, JCP=109.5 Hz); 110.8 (dd, J$_{CF}$=23.3 Hz and 4.0 Hz); 133.2 (t, JCF=14.0 Hz); 134.0 (t, JCF=8.1 Hz); 154.7 (dd, J$_{CF}$=246.6 Hz and 5.4 Hz); 171.4; 172.9. $^{31}$P NMR (200 MHz; D$_2$O) δ (ppm): 41.5 (s). $^{19}$F NMR (376 MHz: D$_2$O) δ (ppm): −129.0 (s) MS (ESI) m/z: 384 [M+H$^+$]. HPLC: t$_R$=10.1 min

Derivative 29

2-amino-4-(((4-(1-carboxyethoxy)phenyl)(hydroxy)methyl)(hydroxy)phosphoryl)butanoic acid The compound was prepared according to general procedure C applied to the protected derivative. The purification was performed using a Dowex AG 50W-X4 cation exchange resin column (Fr, 50-100 mesh, water elution). 259 mg of pure derivative 29 were obtained (26% yield in 2 steps). $^1$H NMR (250 MHz, D$_2$O): δ 1.52 (d, J=7 Hz, 3H), 1.69 (m, 2H), 2.04 (m, 2H), 3.93 (m, 1H), 4.80 (d, J=8 Hz, 1H), 4.85 (q, J=7 Hz, 1H), 6.89 (d, J=9 Hz, 2H), 7.30 (d, J=9 Hz, 2H). $^{31}$P NMR (101 MHz, D$_2$O): δ 40.8 $^{13}$C NMR (126 MHz, D$_2$O): δ 19.0, 23.3 (d, J=85 Hz), 24.3, 54.9 (d, J=13 Hz), 73.2 (d, J=108 Hz), 73.9, 116.3, 129.9, 131.9, 157.8, 173.3, 178.0. MS (ESI): m/z 361.9 [M+H]$^+$. HPLC-MS t$_R$=8.43 min.

Derivative 30

[((3S)-3-Amino-3-carboxy)propyl][(4-(carboxymethoxy)phenyl)methyl]phosphinic Acid (Derivative 30)

The protected derivative was deprotected according to general procedure C. 54.0 mg of pure product derivative 30 were obtained (16% yield, 2 steps). $^1$H NMR (500 MHz, D$_2$O): δ 1.70-190 (m, 2H), 2.03-2.10 (m, 2H), 3.13 (d, J=16.5 Hz, 2H), 4.04 (t, J=6.0 Hz, 1H), 4.67 (s, 2H), 6.91 (d, J=8.5 Hz, 2H), 7.19 (2d, J=8.5 Hz, 2H). $^{31}$P NMR (101 MHz, D$_2$O): δ 60.8. $^{13}$C NMR (126 MHz, D$_2$O): δ 24.0, 24.6 (d, J=92 Hz), 36.7 (d, J=88 Hz), 54.4 (d, J=15 Hz), 66.3, 116.4, 126.4, 132.4, 132.5, 157.7, 172.6, 174.7. MS (ESI): m/z 330.2 (M−1). HPLC-MS: t$_R$=8.02 min. HPLC (RP Polar, elution water/acetonitrile/formic acid 900:100:1, detection λ=240/270 nm): t$_R$=8.3 min. [α]$_D^{20}$: +7.8 (H$_2$O, c 0.2).

Derivative 31

2-amino-4-((4-(carboxymethoxy)-3-methoxybenzyl)(hydroxy)phosphoryl)butanoic acid The compound was prepared according to general procedure C applied to the protected derivative. The purification was performed using a Dowex AG 50W-X4 cation exchange resin column (H$^+$, 50-100 mesh, water elution). 55 mg of pure derivative 31 were obtained (18% yield in 2 steps). $^1$H NMR (500 MHz, D$_2$O): δ 1.64 (m, 2H), 2.01 (m, 2H), 2.96 (d, J=17 Hz, 2H), 3.78 (s, 3H), 3.88 (t, J=6 Hz, 1H), 4.59 (s, 2H), 6.72 (d, J=8 Hz, 1H), 6.77 (d, J=8 Hz, 1H), 6.88 (s, 1H). $^{31}$P NMR (101 MHz, D$_2$O): δ 44.1 $^{13}$C NMR (126 MHz, D$_2$O): δ 24.6, 25.4 (d, J=92 Hz), 37.9 (d, J=87 Hz), 55.0 (d, J=14 Hz), 57.2, 67.0, 114.9, 115.3, 123.5, 128.7, 146.6, 149.7, 173.5, 174.8. MS (ESI): m/z 362.0 [M+H]$^+$ 360.1 [M−H]$^-$. HPLC MS t$_R$=10.27 min. [α]$_D^{20}$+10.8 (H$_2$O, c 1.0).

Derivative 32

2-amino-4-((4-(carboxymethoxy)-3-(trifluoromethoxy)benzyl)(hydroxy)phosphoryl)butanoic acid The compound was prepared according to general procedure C applied to the protected derivative. The purification was performed using a Dowex AG 50W-X4 cation exchange resin column (H$^+$, 50-100 mesh, water elution). Another purification was made on an anion exchange chromatography (Dowex AG 1-X4, AcO$^-$, 200-400 mesh). The resin was first eluted with freshly boiled and cooled water, then with formic acid 3M. 27 mg of pure derivative 32 were obtained (17% yield in 2 steps). $^1$H NMR (500 MHz, D$_2$O): δ 1.78 (m, 2H), 2.03 (m, 2H), 3.12 (d, J=17 Hz, 2H), 4.01 (t, J=6 Hz, 1H), 4.80 (s, 2H), 6.98 (d, J=9 Hz, 1H), 7.1 (d, J=8 Hz, 1H), 7.2 (s, 1H). $^{31}$P NMR (101 MHz, D$_2$O): δ 48.2 $^{13}$C NMR (126 MHz, D$_2$O): δ 23.9, 24.8 (d, J=93 Hz), 36.6 (d, J=88 Hz), 54.3 (d, J=15 Hz), 67.1, 116.4, 121.8 (d, J=256 Hz), 125.5 (d, J=4 Hz), 127.5 (d, J=8 Hz), 130.8 (d, J=9 Hz), 139.0, 149.9, 172.5, 174.0 MS (ESI): m/z 416.0 [M+H]$^+$. HPLC MS t$_R$=23.35 min. [α]$_D^{20}$+9.2 (H$_2$O, c 1.0).

Derivative 33

2-amino-4-((4-(carboxymethoxy)-3-(trifluoromethyl)benzyl)(hydroxy)phosphoryl)butanoic acid The compound was prepared according to general procedure C applied to the protected derivative. The purification was performed using a Dowex AG 50W-X4 cation exchange resin column (H$^+$, 50-100 mesh, water elution). Another purification was made on an anion exchange chromatography (Dowex AG 1-X4, AcO$^-$, 200-400 mesh). The resin was first eluted with freshly boiled and cooled water, then with formic acid 2.5M. 38 mg of pure derivative 33 were obtained (12% yield in 2 steps). $^1$H NMR (250 MHz, D$_2$O): δ 1.64 (m, 2H), 2.01 (m, 2H), 3.00 (d, J=16 Hz, 2H), 3.93 (t, J=6 Hz, 1H), 4.74 (s, 2H), 6.97 (d, J=9 Hz, 1H), 7.37 (d, J=8 Hz, 1H), 7.49 (s, 1H). $^{31}$P NMR (101 MHz, D$_2$O): δ 43.2 $^{13}$C NMR (126 MHz, D$_2$O): δ 24.5, 25.5 (d, J=92 Hz), 37.3 (d, J=86 Hz), 55.0 (d, J=15 Hz), 67.2, 115.4, 119.7 (d, J=29 Hz), 124.9 (d, J=272 Hz), 127.8, 129.6, 136.2, 167.2, 173.3, 174.4 MS (ESI): m/z 399.9 [M+H]$^+$. HPLC MS $t_R$=21.72 min. $[α]_D^{20}$+8.0 (H$_2$O, c 1.0).

Derivative 34

2-amino-4-((4-(carboxymethoxy)-3-fluoro-5-methoxybenzyl)(hydroxy)phosphoryl)butanoic acid The compound was prepared according to general procedure C applied to the protected derivative. The purification was performed using a Dowex AG 50W-X4 cation exchange resin column (H$^+$, 50-100 mesh, water elution). 70 mg of pure derivative 34 were obtained (31% yield in 2 steps). $^1$H NMR (250 MHz, D$_2$O): δ 1.64 (m, 2H), 2.03 (m, 2H), 2.98 (d, J=17 Hz, 2H), 3.85 (s, 3H), 3.90 (t, J=6 Hz, 1H), 4.68 (s, 2H), 6.73 (d, J=11 Hz, 1H), 6.78 (s, 1H). $^{31}$P NMR (101 MHz, D$_2$O): δ 41.0 $^{13}$C NMR (126 MHz, D$_2$O): δ 24.6, 25.6 (d, J=92 Hz), 38.3 (d, J=86 Hz), 55.0 (d, J=15 Hz), 57.7, 71.1, 111.3, 111.5, 131.6, 134.3, 153.8, 156.1 (d, J=245), 173.4, 174.8. MS (ESI): m/z 380.0 [M+H]$^+$. HPLC MS: $t_R$=11.91 min. $[α]_D^{20}$+8.4 (H$_2$O, c 1.0).

Derivative 35

2-amino-4-((4-(carboxymethoxy)-3-chloro-5-methoxybenzyl)(hydroxy)phosphoryl)butanoic acid The compound was prepared according to general procedure C applied to the protected derivative. The purification was performed using a Dowex AG 50W-X4 cation exchange resin column (H$^+$, 50-100 mesh, water elution). 6 mg of pure derivative 35 were obtained (1% yield in 2 steps). $^1$H NMR (500 MHz, D$_2$O): δ 1.63 (m, 2H), 2.03 (m, 2H), 2.98 (d, J=17 Hz, 2H), 3.83 (s, 3H), 3.90 (t, J=6 Hz, 1H), 4.61 (s, 2H), 6.90 (s, 1H), 6.93 (s, 1H). $^{31}$P NMR (101 MHz, D$_2$O): δ 40.4 $^{13}$C NMR (126 MHz, D$_2$O): δ 24.8, 25.8 (d, J=91 Hz), 38.5 (d, J=88 Hz), 55.3 (d, J=15 Hz), 57.6, 70.9, 114.6, 124.0, 128.3, 133.1, 142.6, 154.0, 173.8, 174.8. MS (ESI): m/z 395.9 (100%), 397.9 (32%), 398.9 (6%) [M+H]$^+$. HPLC MS $t_R$=17.49 min. $[α]_D^{20}$+1.1 (H$_2$O, c 0.2).

Agonist activities (EC50) of derivatives 1 to 35 have been determined for group III metabotropic glutamate receptors (mGlu4, mGlu6, mGlu7 and mGlu8) expressed in transfected cells by measuring the ligand-induced intracellular calcium release via the fluorescent probe Fluo4-AM. The EC50's are compared to those of L-AP4 (L-2-amino-4-phosphonobutyric acid) used as a reference.

TABLE 1

| reference | structure | mGlu4 EC$_{50}$ μM (n) | mGlu8 EC$_{50}$ μM (n) | mGlu8/4 EC$_{50}$ ratio | mGlu6 EC$_{50}$ μM (n) | mGlu7 EC$_{50}$ μM (n) | mGlu7/4 EC$_{50}$ ratio |
|---|---|---|---|---|---|---|---|
| L-AP4 | 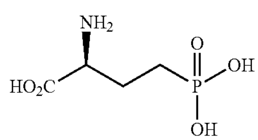 | 0.13 ± 0.02 (34) | 0.29 ± 0.07 (44) | 2 | 1.03 ± 0.27 (7) | >100 (5) | >1000 |
| Derivative 2 | 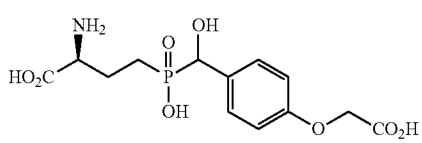 [SMILES: N[C@@H](CCP(=O)(O)C(O)c1ccc(OCC(=O)O)cc1)C(=O)O] | 0.11 ± 0.02 (30) | 29.2 ± 4.2 (27) | 256 | 4.2 ± 0.6 (14) | 11.6 ± 1.9 (19) | 100 |
| Derivative 3 | 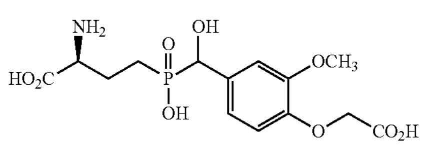 [SMILES: COc1cc(C(O)P(=O)(O)CC[C@H](N)C(=O)O)ccc1OCC(=O)O] | 0.10 ± 0.02 (3) | 18.4 ± 2.4 (3) | 182 | 4.7 ± 3.4 (2) | 11.5 ± 4.2 (3) | 115 |
| Derivative 4 | 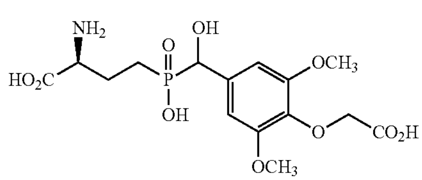 [SMILES: COc1cc(C(O)P(=O)(O)CC[C@H](N)C(=O)O)cc(OC)c1OCC(=O)O] | 0.5 ± 0.12 (5) | 27.2 ± 4.0 (5) | 56 | 9 ± 0.8 (3) | 127 ± 24 (6) | 254 |
| Derivative 5 | 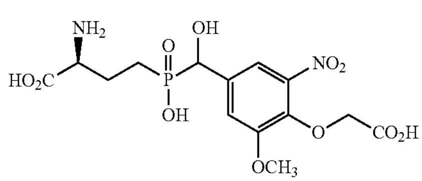 [SMILES: COc1cc(C(O)P(=O)(O)CC[C@H](N)C(=O)O)cc([N+](=O)[O-])c1OCC(=O)O] | 0.28 ± 0.05 (3) | 3.72 ± 0.31 (3) | 13 | 5.95 ± 0.79 (3) | >100 (2) | >350 |

TABLE 1-continued

| reference | structure | mGlu4 EC$_{50}$ μM (n) | mGlu8 EC$_{50}$ μM (n) | mGlu8/4 EC$_{50}$ ratio | mGlu6 EC$_{50}$ μM (n) | mGlu7 EC$_{50}$ μM (n) | mGlu7/4 EC$_{50}$ ratio |
|---|---|---|---|---|---|---|---|
| Derivative 6 | 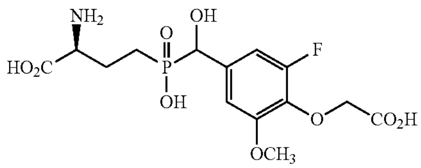 [SMILES: COc1cc(C(O)P(=O)(O)CC[C@H](N)C(=O)O)cc(F)c1OCC(=O)O] | 0.08 ± 0.02 (3) | 10.3 ± 1.3 (3) | 129 | — | 3.5 ± 1.3 (3) | 44 |
| Derivative 7 | 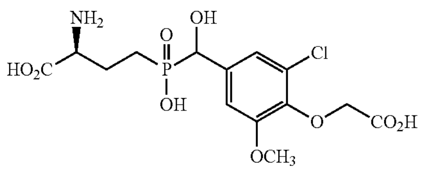 [SMILES: COc1cc(C(O)P(=O)(O)CC[C@H](N)C(=O)O)cc(Cl)c1OCC(=O)O] | 0.13 ± 0.02 (6) | 44 ± 7 (6) | 341 | — | 11.4 ± 0.1 (3) | 88 |
| Derivative 8 | 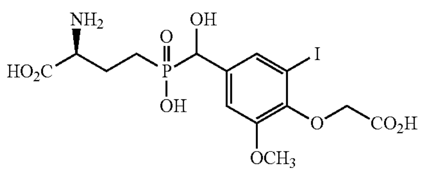 [SMILES: COc1cc(C(O)P(=O)(O)CC[C@H](N)C(=O)O)cc(I)c1OCC(=O)O] | 0.15 ± 0.03 (6) | 28 ± 4 (6) | 193 | — | 6.6 ± 1.5 (3) | 44 |
| Derivative 9 | 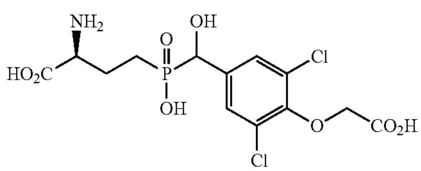 [SMILES: N[C@@H](CCP(=O)(O)C(O)c1cc(Cl)c(OCC(=O)O)c(Cl)c1)C(=O)O] | 0.38 ± 0.09 (3) | 109 ± 15 (3) | 484 | — | 22.9 ± 7.8 (3) | 60 |
| Derivative 10 | 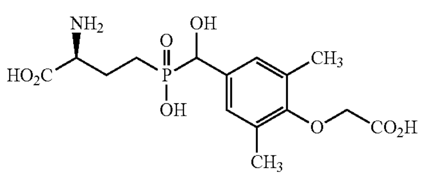 [SMILES: Cc1cc(C(O)P(=O)(O)CC[C@H](N)C(=O)O)cc(C)c1OCC(=O)O] | 0.53 ± 0.12 (3) | 21.9 ± 6.3 (3) | 41 | 18.4 ± 35 (1) | 51.6 ± 16.1 (3) | 97 |
| Derivative 11 | 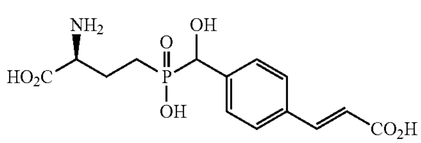 [SMILES: N[C@@H](CCP(=O)(O)C(O)c1ccc(/C=C/C(=O)O)cc1)C(=O)O] | 0.48 ± 0.15 (3) | 49 ± 22 (4) | 103 | 3.8 ± 0.27 (2) | N.E. | >100 |
| Derivative 12 | 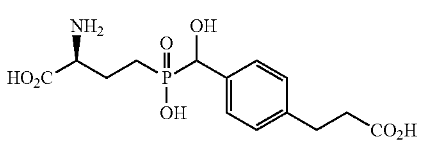 [SMILES: N[C@@H](CCP(=O)(O)C(O)c1ccc(CCC(=O)O)cc1)C(=O)O] | 0.98 ± 0.18 (6) | 48.7 ± 9.6 (6) | 50 | — | 37 ± 5 (3) | 38 |
| Derivative 13 | 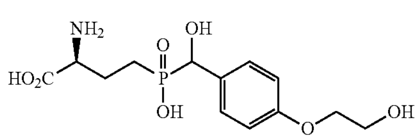 [SMILES: N[C@@H](CCP(=O)(O)C(O)c1ccc(OCCO)cc1)C(=O)O] | 12.2 ± 0.1 (3) | 28 ± 6 (2) | 2.3 | 54 ± 0.0 (2) | N.E. (2) | >100 |
| Derivative 14 | 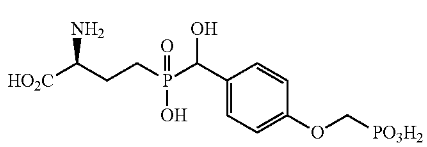 | 0.37 ± 0.12 (4) | 112 ± 46 (4) | 303 | — | 34 ± 10 (4) | 92 |

TABLE 1-continued

| reference | structure | mGlu4 EC$_{50}$ μM (n) | mGlu8 EC$_{50}$ μM (n) | mGlu8/4 EC$_{50}$ ratio | mGlu6 EC$_{50}$ μM (n) | mGlu7 EC$_{50}$ μM (n) | mGlu7/4 EC$_{50}$ ratio |
|---|---|---|---|---|---|---|---|
| Derivative 15 | 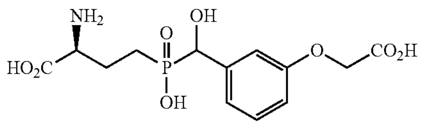 [SMILES: N[C@@H](CCP(=O)(O)C(O)c1cccc(OCC(=O)O)c1)C(=O)O] | 7.6 ± 2.0 (3) | 71 ± 25 (3) | 9.4 | — | — | — |
| Derivative 16 | Dia I | 4.9 ± 1.0 (4) | 36 ± 18 (4) | 7.4 | — | — | — |
| Derivative 17 | Dia II | 13.0 ± 2.9 (3) | 29.3 ± 7.2 (3) | 2.3 | — | — | — |
| Derivative 18 | 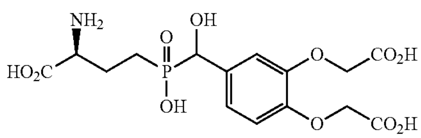 [SMILES: N[C@@H](CCP(=O)(O)C(O)c1ccc(OCC(=O)O)c(OCC(=O)O)c1)C(=O)O] | 2.5 ± 1.1 (3) | 14.1 ± 7.3 (3) | 6 | — | — | — |
| Derivative 19 | 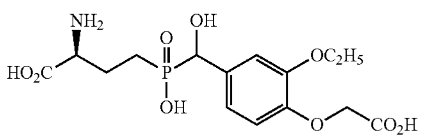 [SMILES: CCOc1cc(C(O)P(=O)(O)CC[C@H](N)C(=O)O)ccc1OCC(=O)O] | 1.67 ± 0.33 (3) | 25.0 ± 6.0 (3) | 15 | — | 60.2 ± 10.6 (3) | 36 |
| Derivative 20 | 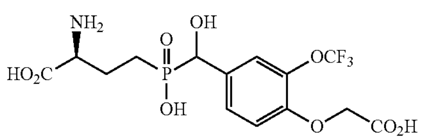 [SMILES: N[C@@H](CCP(=O)(O)C(O)c1ccc(OCC(=O)O)c(OC(F)(F)F)c1)C(=O)O] | 0.06 ± 0.02 (3) | 55.6 ± 12.0 (3) | 927 | — | 1.97 ± 0.34 (3) | 33 |
| Derivative 21 | 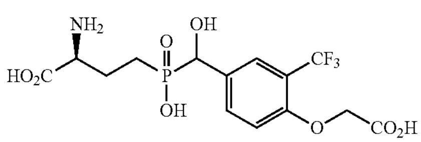 [SMILES: N[C@@H](CCP(=O)(O)C(O)c1ccc(OCC(=O)O)c(C(F)(F)F)c1)C(=O)O] | 0.90 ± 0.06 (3) | 6.86 ± 1.83 (3) | 8 | — | 35.5 ± 4.0 (3) | 39 |
| Derivative 22 | 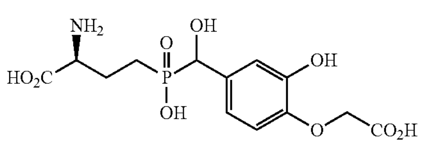 [SMILES: N[C@@H](CCP(=O)(O)C(O)c1ccc(OCC(=O)O)c(O)c1)C(=O)O] | 1.1 ± 0.4 (3) | 34 ± 19 (3) | 31 | — | 15 ± 3.6 (3) | 14 |
| Derivative 23 | 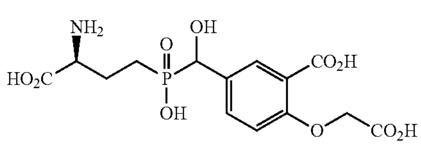 [SMILES: N[C@@H](CCP(=O)(O)C(O)c1ccc(OCC(=O)O)c(C(=O)O)c1)C(=O)O] | 4.0 ± 0.6 (3) | 7.4 ± 1.2 (3) | 1.9 | — | 65 ± 13 (3) | 16 |
| Derivative 24 | 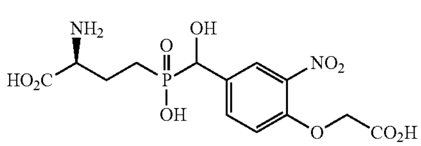 [SMILES: N[C@@H](CCP(=O)(O)C(O)c1ccc(OCC(=O)O)c([N+](=O)[O-])c1)C(=O)O] | 0.26 ± 0.07 (3) | 1.59 ± 0.82 (3) | 6.1 | — | 11.2 ± 3.9 (3) | 43 |

TABLE 1-continued

| reference | structure | mGlu4 EC$_{50}$ μM (n) | mGlu8 EC$_{50}$ μM (n) | mGlu8/4 EC$_{50}$ ratio | mGlu6 EC$_{50}$ μM (n) | mGlu7 EC$_{50}$ μM (n) | mGlu7/4 EC$_{50}$ ratio |
|---|---|---|---|---|---|---|---|
| Derivative 25 | 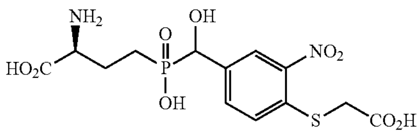 [SMILES: N[C@@H](CCP(=O)(O)C(O)c1ccc(SCC(=O)O)c([N+](=O)[O-])c1)C(=O)O] | 1.10 ± 0.36 (3) | 11.5 ± 5. (4) | 10.4 | — | 15.2 ± 3.9 (4) | 1.4 |
| Derivative 26 | 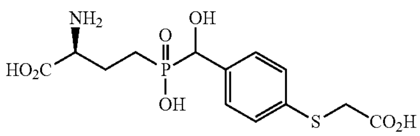 [SMILES: N[C@@H](CCP(=O)(O)C(O)c1ccc(SCC(=O)O)cc1)C(=O)O] | 0.21 ± 0.04 (3) | 1.23 ± 0.48 (3) | 5.9 | — | 13.0 ± 1.1 (3) | 62 |
| Derivative 27 | 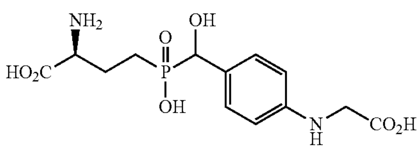 [SMILES: N[C@@H](CCP(=O)(O)C(O)c1ccc(NCC(=O)O)cc1)C(=O)O] | | | | | | |
| Derivative 28 | 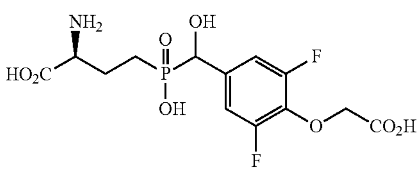 [SMILES: N[C@@H](CCP(=O)(O)C(O)c1cc(F)c(OCC(=O)O)c(F)c1)C(=O)O] | 0.33 ± 0.14 (3) | 27.5 ± 6.7 (3) | 83 | 2.5 ± 0.6 (3) | 3.87 ± 0.45 (3) | 11.7 |
| Derivative 29 | 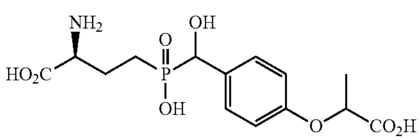 [SMILES: CC(Oc1ccc(C(O)P(=O)(O)CC[C@H](N)C(=O)O)cc1)C(=O)O] | 0.95 ± 0.16 (2) | 14.3 ± 5.6 (3) | 15 | — | 103 ± 7 (3) | 109 |
| Derivative 30 | 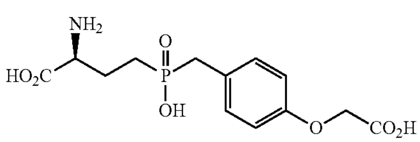 | 1.0 ± 0.2 (5) | >100 (4) | >100 | 13.0 ± 4.0 (3) | >100 (4) | >100 |
| Derivative 31 | 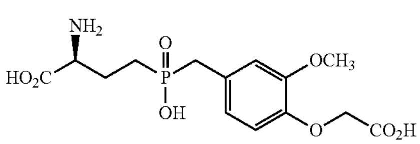 | 7.41 ± 1.55 (3) | >300 (3) | >40 | — | N.E. (3) | |
| Derivative 32 | 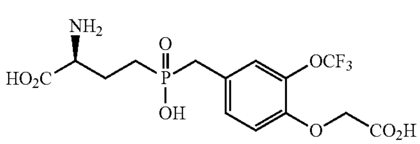 | 1.22 ± 0.15 (3) | >100 (4) | >82 | — | 16.2 ± 3.5 (3) | 13 |
| Derivative 33 | 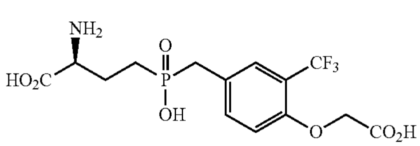 | 62.5 ± 20.5 (3) | >100 (3) | 1.6 | — | 301 ± 73 (3) | 5 |
| Derivative 34 | 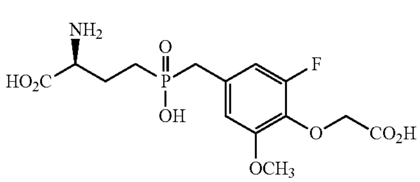 [SMILES: COc1cc(CP(=O)(O)CC[C@H](N)C(=O)O)cc(F)c1OCC(=O)O] | 3.09 ± 0.62 (3) | 9.17 ± 2.37 (3) | 3 | — | 232 ± 85 (3) | 75 |

TABLE 1-continued

| reference | structure | mGlu4 EC$_{50}$ µM (n) | mGlu8 EC$_{50}$ µM (n) | mGlu8/4 EC$_{50}$ ratio | mGlu6 EC$_{50}$ µM (n) | mGlu7 EC$_{50}$ µM (n) | mGlu7/4 EC$_{50}$ ratio |
|---|---|---|---|---|---|---|---|
| Derivative 35 | [structure: NH$_2$, HO$_2$C, P(=O)(OH)CH$_2$-aryl with Cl, OCH$_3$, OCH$_2$CO$_2$H substituents] | 6.20 ± 0.58 (3) | 38.2 ± 7.1 (3) | 6 | — | >300 (3) | >48 |

It results from the examination of the above data that derivatives 2 to 4, 6 to 8 and 20 have a high activity with respect to mGlu4R. At low concentrations, these compounds are mGlu4R selective. Advantageously, derivates 2, 3, 6 to 8 and 20 display a higher affinity on mGlu7 than ever known, then producing an advantagenous synergistic effect at higher concentrations through the activation of both mGlu4 and mGlu7 for pain treatment compared to reference derivative L-AP4. Derivates 4, 5 and 30 are particularly selective for mGlu4, with a decreased activity on mGlu7R compared to the reference derivative.

EXAMPLE 2

Tests In Vivo

Antihyperalgesic Properties

Antihyperalgesic properties of derivative 2 have been tested in vivo on healthy animals and animal models for inflammatory (inflammation caused by injection of carrageenan) or neuropathic (chronic constriction of the sciatic nerve) pain.

After the induction period of the neuropathy or inflammation, various amounts of derivative 2 dissolved in serum have been injected in rats, (from 0.5 to 15 µg/rat, i.t. from 1 to 30 mg/kg, i.p.) on time-course of vocalization threshold to paw pressure. The results obtained on healthy animals are given on FIG. 1. They are expressed by the time course curves of means+/−SEM of vocalization threshold in grams (n=6-8 rats per group) (A) or by the area under the curve (B). Morphine (10 µg/rat, i.t.) is used as a positive control. Significantly different from the vehicle group, ***P<0.001.

As previously shown for other agonists of mGluRs of group III, derivative 2 does not modify the perception of the mechanical acute pain in healthy animal (FIG. 1).

Figure 2:
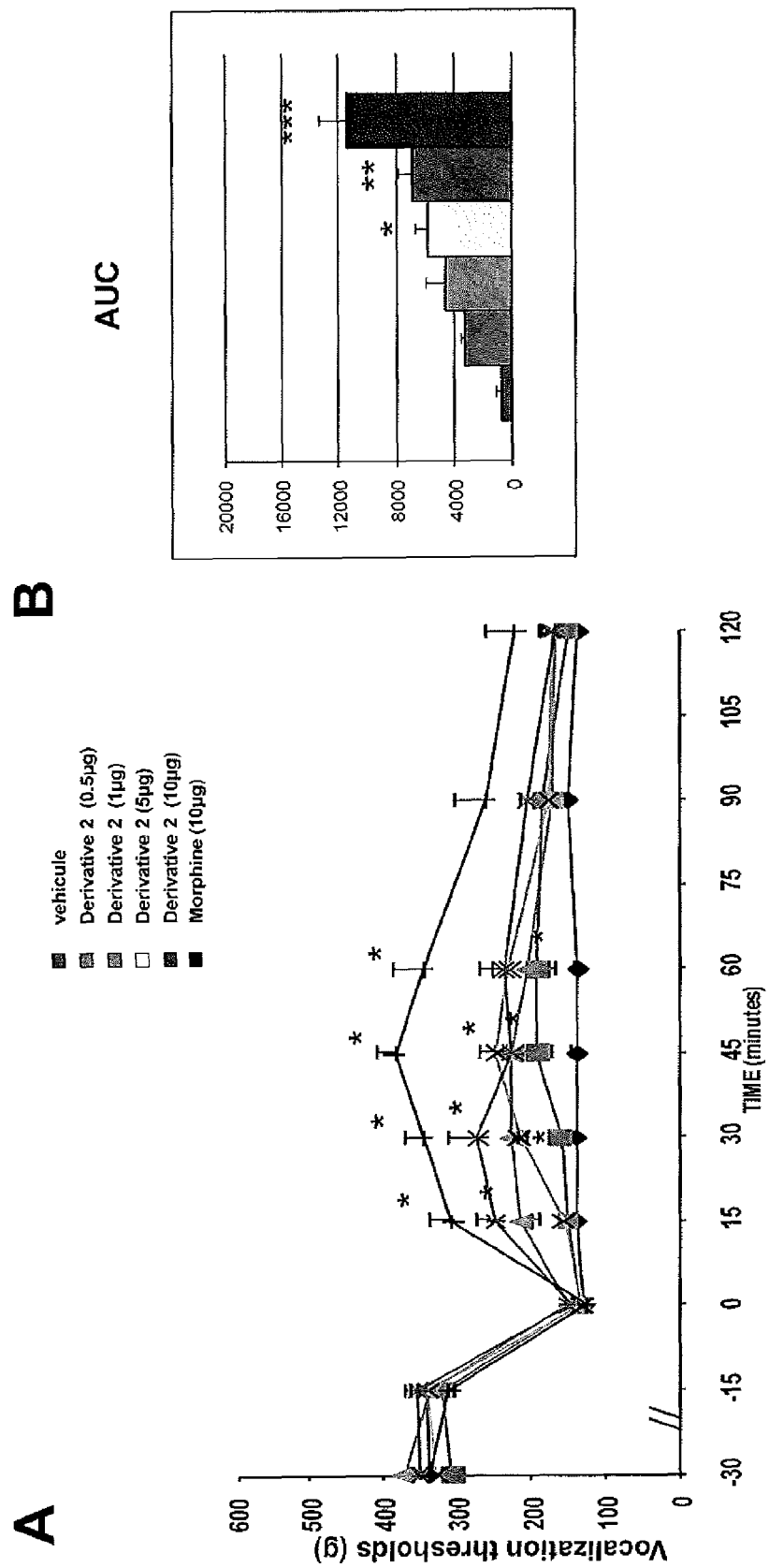
FIG. 2: the antihyperalgesic effect of intrathecal administration of derivative 1 on the vocalization threshold to paw pressure in the carrageenan inflammatory pain model.
Figure 3:
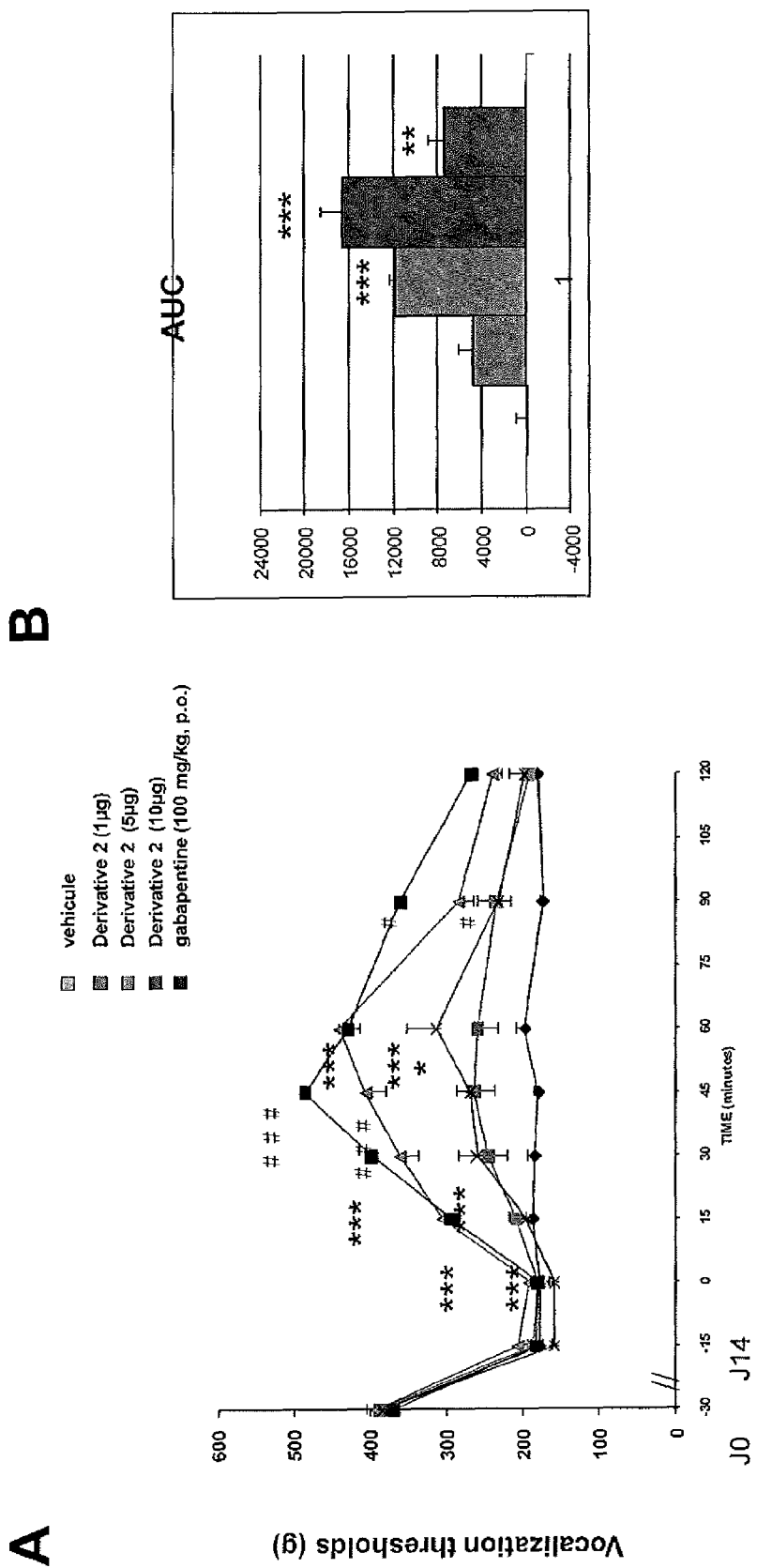
FIG. 3: the antihyperalgesic effect of intrathecal administration of derivative 1 on the vocalization threshold to paw pressure in the CCI neuropathic pain model.

On the contrary, derivative 2 abolishes the excess of mechanical pain observed on animals with neuropathic or inflammatory pains in a dose and time-dependent manner (FIGS. 2 and 3).

FIG. 2 illustrates the effect of intrathecal administration of derivative 2 on the vocalization threshold to paw pressure in the carrageenan inflammatory pain model (effect of derivative 2 (0.5, 1, 5, 10 µg/rat, i.t.) on time-course of vocalization threshold to paw pressure). Morphine (10 µg/rat, i.t.) is used as a positive control. Results are expressed by the time course curves of means+/−SEM of vocalization threshold in grams (n=6-8 rats per group) (A) or by the area under the curve (B), significantly different from the vehicle group, *P<0.05, P<0.01, *P<0.001. Moreover, while derivative 2 also dose-dependently reduced the mechanical hypersensitivity measured using Von Frey filaments eliciting innocuous to noxious mechanical stimuli in a model of inflammation induced by carrageenan in C57BL6 mice, intrathecal administration of derivative 2 (10 µg/mice, i.t.) is significantly decreased in mice lacking mGluR4 receptor as compared to their wild-type littermates in this inflammatory pain model (carrageenan) FIG. 3.

Figure 4:
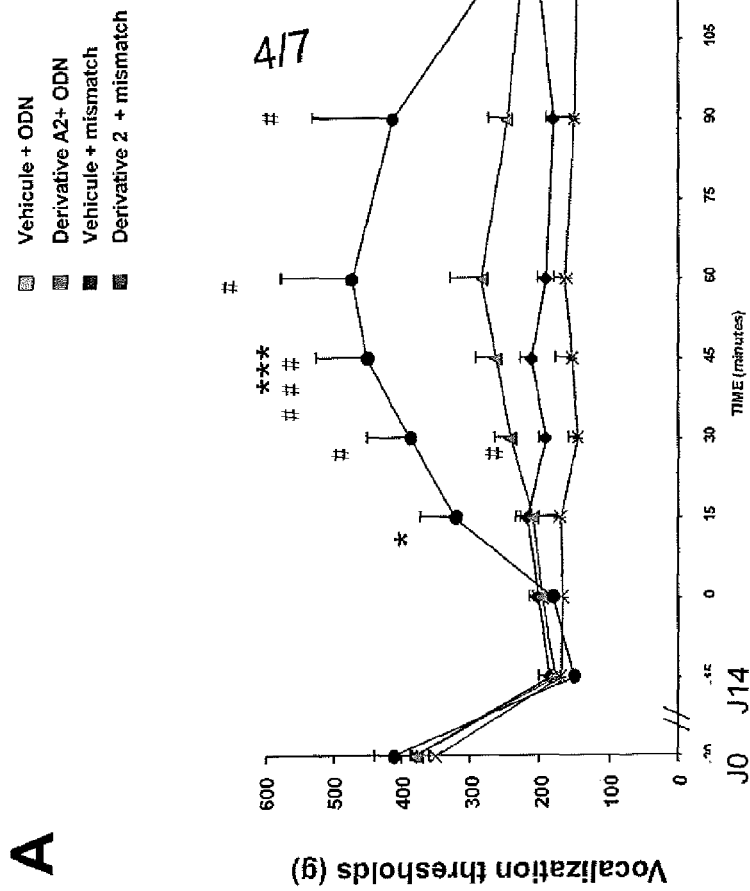
FIG. 4: the antihyperalgesic effect of intrathecal administration of derivate A on the vocalization threshold to paw pressure in the CCI neuropathic model (decrease when ODN against mGlu4R are injected)

FIG. 4 illustrates the effect of intrathecal administration of derivative 2 on the vocalization threshold to paw pressure in the CCI neuropathic pain model (effect of derivative 2 (1, 5, 10 µg/rat, i.t.) on time-course of vocalization threshold to paw pressure). Gabapentin (100 mg/kg, p.o.) is used as a positive control. Results are expressed by the time course curves of means+/−SEM of vocalization threshold in grams (n=7-8 rats per group) (A) or by the area under the curve (B), significantly different from the vehicle group, P<0.01, *P<0.001.

The antihyperalgesic effect of derivative 2 is significantly higher than the one of gabapentine (100 mg/kg, per os) used as control in the neuropathy model and close to the one of morphine used as control on the inflammatory pain.

The effect of intrathecal administration of derivative 2 (10 µg/rat, i.t.) on the vocalization threshold to paw pressure in the CCI neuropathic pain model after mGluR4 or mismatch ODN treatment is illustrated by FIG. 4. Results are expressed by the time course curves of means+/−SEM of vocalization threshold in grams (n=5-8 rats per group) (A) or by the area under the curve (B), significantly different from the considered group, *P<0.05, ***P<0.001.

On neuropathic rats treated with antisens oligonucleotides against mGlu4, the antihyperalgesic effect of derivative 2 is significantly reduced with respect to the control conditions (saline or "mismatch" antisens targeting no target), illustrating that a great part of derivative 2 effect is induced via mGlu4 R.

Figure 5:
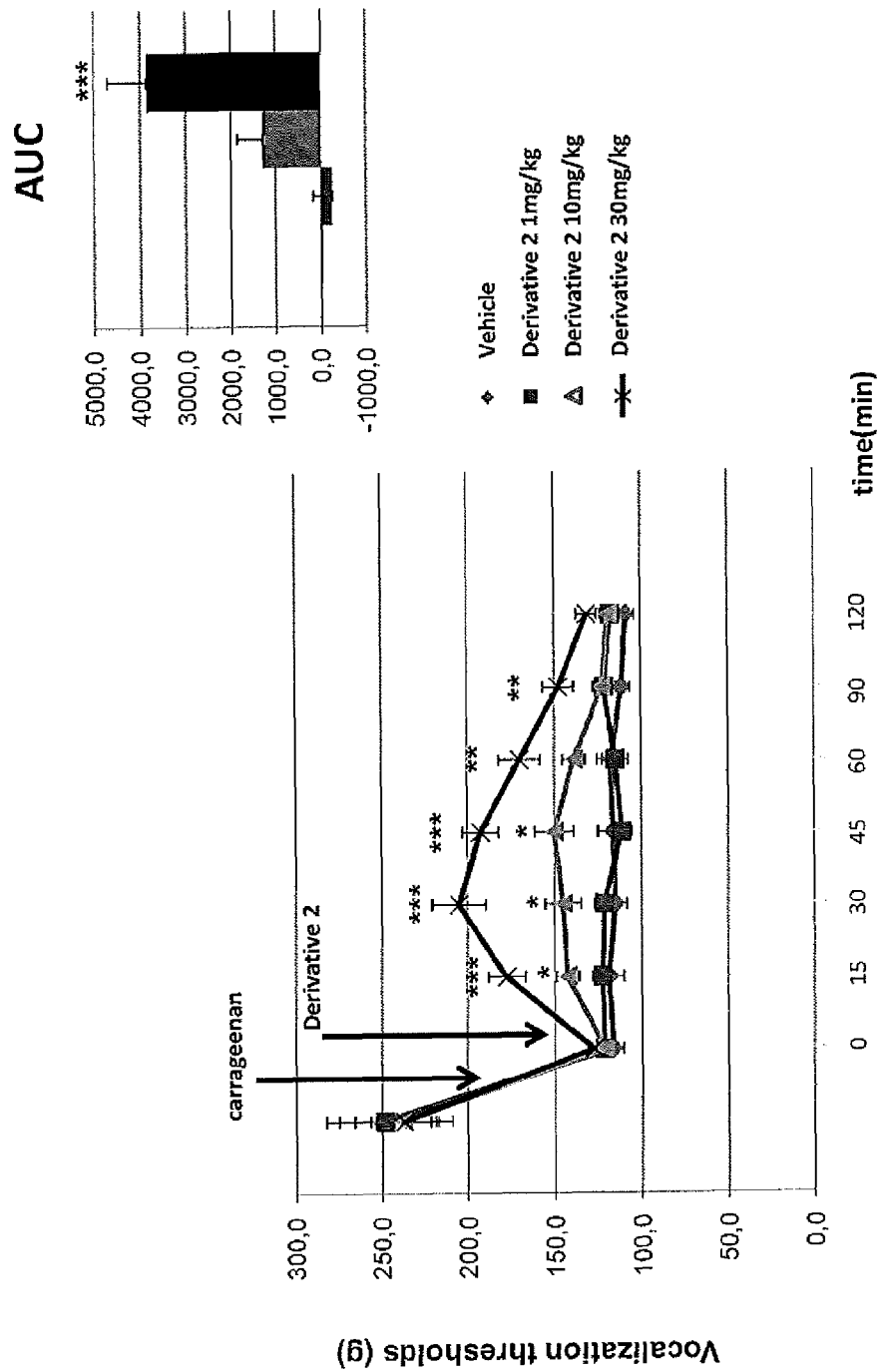
FIG. 5: the antihyperalgesic effect of derivative 1 (i.p.) in a rat model of inflammatory pain ("carrageenan") treated.
Figure 6:
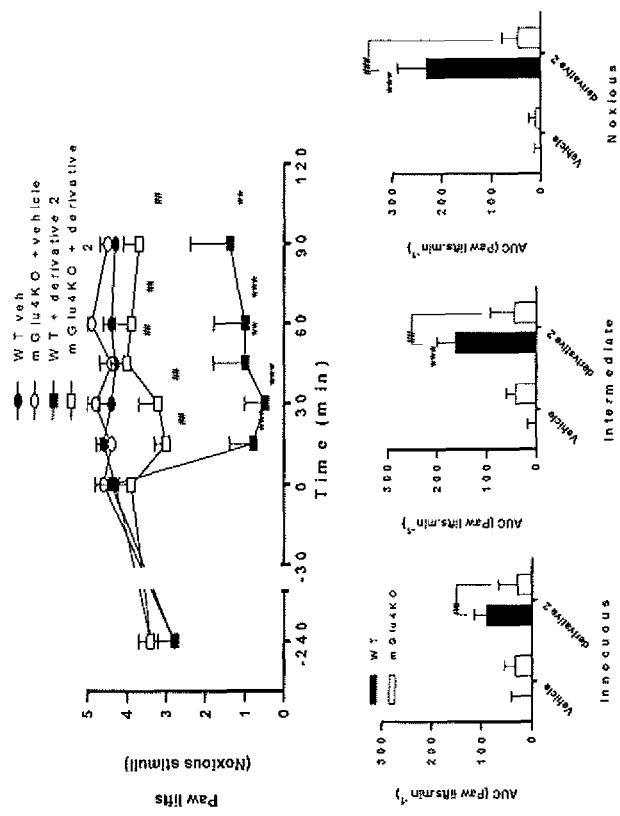
FIG. 6: the mechanical antihyperalgesic effect of derivative 2 is profoundly impaired in inflamed genetically modified mice lacking the gene encoding for the mglu4 receptor
Figure 7:
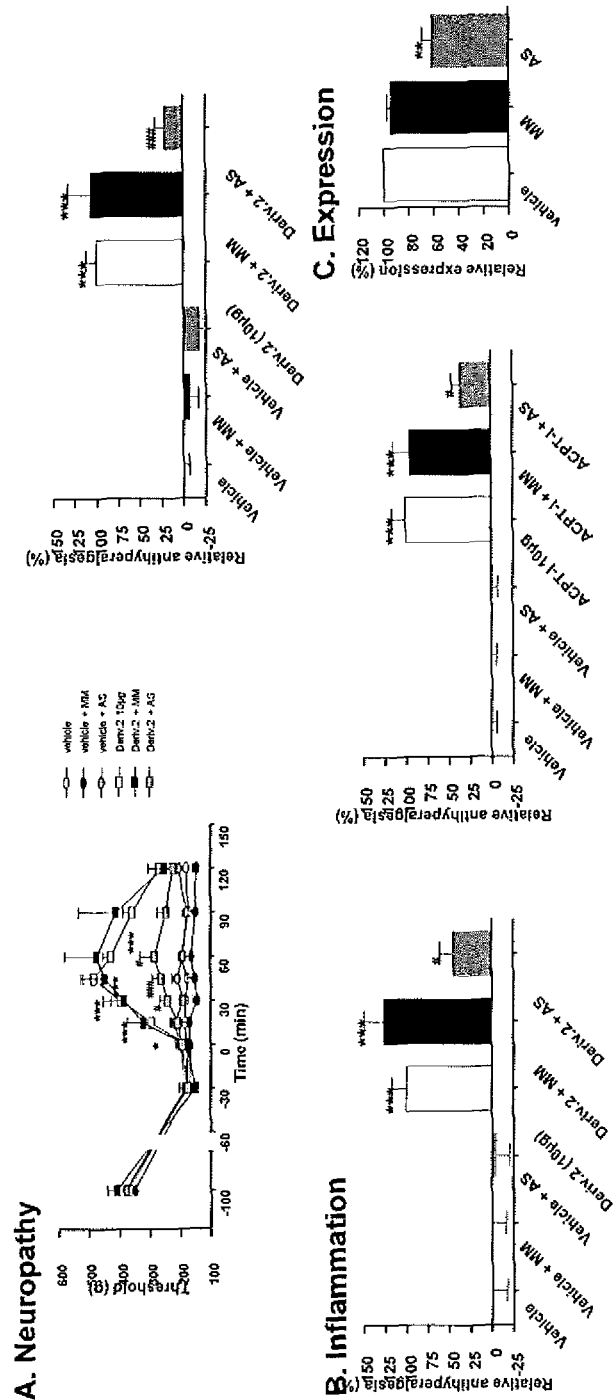
FIG. 7: the knockdown of spinal mGlu$_4$ expression by antisense oligonucleotides reduces mechanical antihyperalgesia induced by derivative 2 or ACPT-I

FIG. 5 illustrates the effect of systemic injection of derivative 2 on the vocalization threshold to paw pressure in a rat model of inflammatory pain (carageenan) (effect of derivative 2 (1, 10, 30 mg/kg, i.p.)) on time-course of vocalization threshold to paw pressure). Results are expressed by the time course curves of means+/−SEM of vocalization threshold in grams (n=7-8 rats per group) (A) or by the area under the curve (B), significantly different from the vehicle group, *P<0.05, P<0.01, *P<0.001.

The above results demonstrate the strong antihyperalgesic potential of derivative 2 in chronic pains of inflammatory or neuropathic origin.

Material & Methods

Animals

Adult male Sprague-Dawley rats weighting 175-200 g were purchased from Charles River. C57/BL6 mice were from Elevage Janvier, and homozygous mGlu4 (−/−) and wild-type (+/+) littermates were generated from crosses between heterozygous animals. Animals were housed under controlled environmental conditions (22° C.; 55% humidity) and kept under a 12/12 h light/dark cycle, with food and water ad libitum for a week prior to start the experiments in order to acclimatize. Animal care and experiments were carried out in accordance with the Committee for Research and Ethical Issues of the IASP (Zimmermann M., 1983; Goudet C., 2008).

Mechanical Testing in Rats Using the Paw Pressure Test

The animals were submitted to the paw pressure test previously described by Randall and Selitto (1957). Nociceptive thresholds, expressed in grams (g), were measured with a Ugo Basile analgesimeter (Apelex, tip diameter of the probe: 1 mm, weight: 30 g) by applying an increasing pressure to the right hind paw of rats until a squeak (vocalization threshold) was obtained (cut-off was 750 g except carrageenan treated animals for which the cut-off was 500 g). The treatments were done after the measurement of two consecutive stable vocalization threshold values and their effects were assessed 15, 30, 45, 60, 90, and 120 min after.

Mechanical Testing in Mice Using the von Frey Test

Mechanical allodynia and hyperalgesia were assessed using the von Frey hair filaments of 3 different bending forces (0.07 g, 0.6 g, 1.4 g). For each filament, 5 stimuli were applied with an interval of 3-5 s.

Persistent Pain Models: Inflammatory and Neuropathic Pain Models

Carrageenan-Induced Mechanical Hyperalgesia

Thresholds to mechanically induced vocalization were assessed with rats presenting an hyperalgesia elicited by a subcutaneous injection of 2-carrageenan (200 µg) into the right hind paw (200 µL). Four hours later, vocalization thresholds were significantly decreased from 336±6 g to 137±2 g.

Chronic Constriction Injury (CCI) Model

Unilateral peripheral mononeuropathy was induced according to the method described by Bennett and Xie (1988). Briefly, after determining vocalization thresholds, rats were anesthetized with sodium pentobarbital (50 mg/kg i.p.) and four chromic gut (5-0) ligatures were tied loosely (with about 1-mm spacing) around the right common sciatic nerve. The nerve was constricted to a barely discernible degree, so that circulation through the epineurial vasculature was not interrupted. Only animals presenting a decrease ≥15% of the presurgery value of vocalization threshold were selected, i.e., 90% of ligated animals (presurgery value: 379±7 g, pre-drug value: 188±7 g).

Experimental Procedure and Drugs

Treatment Protocol

For all experiments, treatments were randomized and administered according to the method of blocks in order to assess the effect of the different treatments at the same time interval to avoid uncontrolled influences (one block includes a number of animals corresponding to the number of the different treatments administered; all animals in a same block are tested in the same short laps of time; the number of blocks corresponds to the number of animals per treatment). Different animals were used for each experiment (n=6-10 per treatment, according to the experiments) performed in a blinded manner in a quiet room and animal behaviors were observed by a single experimenter.

Intrathecal Injections

Intrathecal injections were performed, under isoflurane anesthesia (4% induction, 2% maintenance), as previously described (Mestre et al., 1994). Briefly, the anesthetized rat was held in one hand by the pelvic girdle and a 25-gauge X1-inch needle connected to a 25 µL Hamilton syringe was inserted into the subarachnoidal space between lumbar vertebrae L5 and L6, until a tail flick was elicited. The syringe was held in position for few seconds after the injection of a volume of 10 µL/rat.

Drugs

Gabapentin, derivative 2 and morphine were dissolved in saline (0.9% NaCl, B. Braun, Melsungen, Germany). All solutions were prepared immediately prior to injection.

Oligodeoxynucleotides Targeting mGluR4 Subunit

AS ODN was designed based on rat mGluR4 sequence in regions lacking known splice variants. They were synthesized by Eurogentec and sequences were as follows: AS-mGluR4, 5'-CGGATAGAGTTCATGTGG-3'. One ODN with scramble arrangement in the base composition compared to the 18-mer specific as was used as control for sequence-independent effects of ODN treatments. A blast search revealed that this mismatch ODNs were not complementary to any registered nucleotide sequences.

Intrathecal ODN Administration

I.t. administrations of ODNs (12.5 µg/rat) or saline were performed in a volume of 10 µl via direct transcutaneous injection (with a 25-gauge needle connected to a 25 µl Hamilton syringe) between the L5 and L6 dorsal spinous processes (Mestre et al., 1994) under animal anaesthesia with isofluran (3.5%). This treatment was repeated twice daily for 4 days (days 1-4). Pain scores were determined using standard methods in strict conformity with ethical standards (Zimmermann M., 1983) before ODN treatments and then on day 4 in the afternoon. Treatments were randomized and all experiments were performed blind by the same experimenter using the method of equal blocks to avoid any uncontrollable environmental influence that might induce a modification in behavioural response.

Expression of Results and Statistical Analysis

For the mechanical pain test, the results are expressed as vocalization thresholds, in grams (g). To investigate global effects, areas under the time-course curves (AUCs, g·min) of the antihyperalgesic effects were calculated from individual scores at each time, using the trapezoidal method. Data were analyzed by a two-way ANOVA followed, when the F value was significant, by a Dunnett's test, when the time-course of the effects was studied. One-way ANOVA followed by a Student-Newman-Keuls' test was used to analyze the effect of the different treatments determined by the AUCs. The level of statistical significance was set at $p<0.05$.

Pharmacological Assays on Recombinant mGluR5

Metabotropic glutamate receptors were transiently transfected in HEK293 cells by electroporation as described elsewhere (Brabet I. et al., 1998) and plated in 96-well microplates. The high affinity glutamate transporter EAAC1 was co-transfected with the receptor in order to avoid any influence of glutamate released by the cells in the assay medium. In the experiments carried out by the inventors, Group-III mGluRs were co-transfected with a chimeric G-protein which couples the activation of the receptor to the phospholipase-C (PLC) pathway. Thus receptor activation induces production of inositol phosphate (IP) which in turn induces intracellular $Ca^{2+}$ release. Receptor activity was then determined by measurement of the IP production or Ca release as already described (Goudet C. et al., PNAS 2004). For intracellular calcium measurements, cells expressing mGluRs were loaded with Ca2+-sensitive fluorescent dye Fluo-4 AM (Invitrogen, Cergy-Pontoise, France) dissolved in Hanks' balanced salt solution (HBSS, Invitrogen, Cergy-Pontoise, France) containing 2.5 mM Probenicid (Sigma-Aldrich Chemie, Saint-Quentin Fallavier, France) for 1 h at 37° C., then washed and incubated with HBSS containing probenecid. A drug plate was prepared with the various concentrations of agonist to be tested and drug solution was added in each well after 20 s of recording. Fluorescence signals (excitation 485 nm, emission 525 nm) were measured by using the fluorescence microplate reader Flexstation III (Molecular Devices, Saint-Grégoire, France) at sampling intervals of 1.5 s for 60 s. All points are realized in triplicate.

The dose-response curves were fitted using the GraphPad Prism program and the following equation: $y=[(y_{max}-y_{min})/(1+(x/EC_{50})n)]+y_{min}$ where $EC_{50}$ is the concentration of the compound necessary to obtain the half maximal effect and n is the Hill coefficient.

REFERENCES

Bennett G. J. and Xie Y. K., *Pain* 33 (1988), pp. 87-107.

Mestre C., Pelissier T., Fialip J., Wilcox G. and Eschalier A., *J. Pharmacol. Toxicol. Methods* 32 (1994), pp. 197-200.

Zimmermann M., *Pain* 16 (1983), pp. 109-110.

Randall L. O. and Selitto J. J., *Arch. Int. Pharmacodyn. Ther.* 111 (1957), pp. 409-419.

Gomeza, J., Mary, S., Brabet, I., Parmentier, M. L., Restituito, S., Bockaert, J., and Pin, J. P. (1996), *Mol. Pharmacol.* 50, 923-930.

Brabet, I., Parmentier, M. L., De Colle, C., Bockaert, J., Acher, F., and Pin, J. P. (1998), *Neuropharmacology* 37, 1043-1051.

Goudet, C., Gaven, F., Kniazeff, J., Vol, C., Liu, J., Cohen-Gonsaud, M., Acher, F., Prezeau, L., and Pin, J. P. (2004), *Proc. Natl. Acad. Sci. U.S.A.* 101, 378-383.

Selvam et al., *J. of Medicinal Chemistry*, 2010, 53, 2797-2813.

Cuomo, D.; Martella, G.; Barabino, E.; Platania, P.; Vita, D.; Madeo, G.; Selvam, C.; Goudet, C.; Oueslati, N.; Pin, J.-P.; Acher, F.; Pisani, A.; Beurrier, C.; Melon, C.; Kerkerian-Le Goff, L.; Gubellini, P., *J. Neurochem.* 2009, 109, 1096-1105.

Beurrier, C.; Lopez, S.; Révy, D.; Selvam, C.; Goudet, C.; Lhérondel, M.; Paolo Gubellini, P.; Kerkerian-LeGoff, L.; Acher, F.; Pin, J.-P.; Amalric, M., *FASEB J.* 2009, 23, 3619-3628.

Wieronska, J. M.; Stachowicz, K.; A., P.-P.; Acher, F.; Branski, P.; Pilc, A., *Neuropharmacology* 2011, 59, 627-634.

Battistuzzi, G.; Cacchi, S.; Fabrizi, G.; Bernini, R., *Synlett* 2003, 8, 1133-1136.

Giannini, G, Marzi, M.; Pezzi, R.; Brunetti, T.; Battistuzzi, G.; Di Marzo, M.; Cabri, W.; Vesci, L.; Pisano, C., *Bioorg. Med. Chem. Lett.* 2009, 19, 2346-2349.

Goudet, C.; Chapuy, E.; Alloui, A.; Acher, F.; Pin, J.-P.; Eschalier, A., *Pain* 2008, 137, 112-124.

The invention claimed is:

1. Hypophosphorous acid derivatives of formula

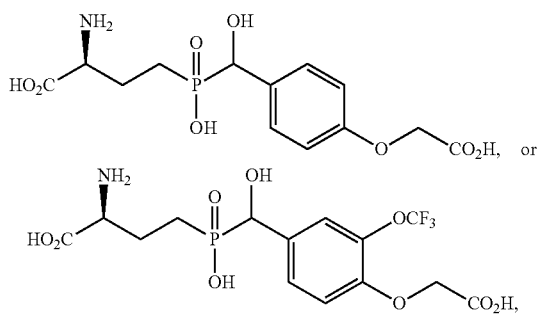

said hypophosphorous acid derivatives being diastereoisomers or enantiomers.

2. A pharmaceutical composition comprising at least one of the hypophosphorous acid derivatives according to claim 1, in combination with a pharmaceutically acceptable carrier.

3. The pharmaceutical composition of claim 2, wherein the at least one hypophosphorous acid derivative simultaneously activates metabotropic glutamate receptor (mGluR) subtypes 4 and 7 for the treatment of neuropathic and inflammatory pain.

4. The pharmaceutical composition of claim 2, wherein the at least one hypophosphorous acid derivative has an $EC_{50}$ with respect to mGluR7 receptors greater than 1 µM.

5. The pharmaceutical composition of claim 2, wherein the at least one hypophosphorous acid derivative has an $EC_{50}$ mGlu8>10 µM, and an $EC_{50}$ mGlu4<0.5 µM.

6. The pharmaceutical composition of claim 2, in a form suitable for oral administration.

7. The pharmaceutical composition of claim 6, comprising 1 to 100 mg of the hypophosphorous acid derivative per dose unit.

8. The pharmaceutical composition of claim 2, in a form suitable for administration by injection.

9. The pharmaceutical composition of claim 8, comprising 1 to 30 mg of the hypophosphorous acid derivative per dose unit.

10. The pharmaceutical composition of claim 6, in the form of a tablet, pill or capsule.

11. The pharmaceutical composition of claim 8, in form of an injectable solution for intravenous, subcutaneous or intramuscular injection.

* * * * *